US011576962B2

(12) United States Patent
Sekikawa

(10) Patent No.: US 11,576,962 B2
(45) Date of Patent: Feb. 14, 2023

(54) CROSS-IMMUNIZING ANTIGEN VACCINE AND METHOD FOR PREPARATION THEREOF

(71) Applicant: Green BioMed, Inc., Tsukuba (JP)

(72) Inventor: Kenji Sekikawa, Ibaraki (JP)

(73) Assignee: Green BioMed, Inc., Ibaraki (JP)

( * ) Notice: Subject to any disclaimer, the term of this patent is extended or adjusted under 35 U.S.C. 154(b) by 114 days.

(21) Appl. No.: 16/956,212

(22) PCT Filed: Dec. 21, 2018

(86) PCT No.: PCT/JP2018/047379
§ 371 (c)(1),
(2) Date: Jun. 19, 2020

(87) PCT Pub. No.: WO2019/124557
PCT Pub. Date: Jun. 27, 2019

(65) Prior Publication Data

US 2021/0069320 A1 Mar. 11, 2021

(30) Foreign Application Priority Data

Dec. 21, 2017 (JP) ............................ JP2017-245606

(51) Int. Cl.

| | |
|---|---|
| ***A61K 39/00*** | (2006.01) |
| ***A61K 39/085*** | (2006.01) |
| ***C07K 14/31*** | (2006.01) |
| ***A61K 39/21*** | (2006.01) |
| ***A61K 38/00*** | (2006.01) |
| ***A61K 39/145*** | (2006.01) |
| ***A61P 31/16*** | (2006.01) |
| ***A61K 39/12*** | (2006.01) |
| ***C07K 14/005*** | (2006.01) |

(52) U.S. Cl.
CPC ............ *A61K 39/145* (2013.01); *A61K 39/12* (2013.01); *A61P 31/16* (2018.01); *C07K 14/005* (2013.01); *A61K 2039/572* (2013.01); *A61K 2039/575* (2013.01); *C07K 2319/40* (2013.01); *C12N 2760/16122* (2013.01); *C12N 2760/16134* (2013.01); *C12N 2770/24122* (2013.01); *C12N 2770/24134* (2013.01)

(58) Field of Classification Search
CPC .......... A61P 37/04; A61P 31/04; A61K 39/00; A61K 39/085; C07K 14/31
See application file for complete search history.

(56) References Cited

U.S. PATENT DOCUMENTS 7,459,160 B2 12/2008 Monath et al.
7,736,642 B2 6/2010 Duke et al.
8,444,995 B2 5/2013 Soloff et al.
8,475,802 B2 7/2013 Stoloff et al.
8,747,861 B2 6/2014 Ben-Yedidia et al.
8,852,914 B2 10/2014 Monath et al.
9,198,964 B2 12/2015 Coller et al.
9,211,323 B2 12/2015 Stinchcomb et al.
9,212,217 B2 12/2015 Robinson et al.
9,365,639 B2 6/2016 Robinson et al.
9,446,116 B2 9/2016 Stoloff et al.
9,452,211 B2 9/2016 Meijberg et al.
9,463,237 B2 10/2016 Falkner et al.
9,637,522 B2 5/2017 Lu et al.
9,708,373 B2 7/2017 Garcia-Sastre et al.
9,889,191 B2 2/2018 Stoloff et al.
9,969,778 B2 5/2018 Meijberg et al.
10,010,600 B2 7/2018 Stinchcomb et al.
10,137,187 B2 11/2018 Coller et al.
10,155,806 B2 12/2018 Robinson et al.
10,172,929 B2 1/2019 Monath et al.
10,179,806 B2 1/2019 Garcia-Sastre et al.
10,279,032 B2 5/2019 Stoloff et al.
10,316,066 B2 6/2019 Tangy et al.
10,329,583 B2 6/2019 Falkner et al.
10,335,480 B2 7/2019 Stoloff et al.

(Continued)

FOREIGN PATENT DOCUMENTS

EP 2 650 362 A2 10/2013
EP 3 111 953 A1 1/2017

(Continued)

OTHER PUBLICATIONS

Noton et al., "Identification of the domains of the influenza A virus M12 matrix protein required for NP binding oligomerization and incorporation into virions", Journal of General Virology, 2007, 88:2280-2290.*

(Continued)

*Primary Examiner* — Barry A Chestnut

(74) *Attorney, Agent, or Firm* — Foley & Lardner LLP

(57) ABSTRACT

The present invention provides a fusion polypeptide that induces a humoral immune response and a cellular immune response to a virus, containing antigens or fragments thereof of the following (a) and (b), and having an oligomerization activity:

(a) an antigen of the virus or a fragment thereof containing a B cell epitope conserved among subtypes of the virus; and (b) an antigen of the virus or a fragment thereof containing a T cell epitope conserved among subtypes of the virus (wherein the antigen(s) or the fragment(s) thereof of (a) and/or (b) have an oligomerization activity, or the fusion polypeptide further contains (c) a polypeptide having an oligomerization activity in addition to the antigens or the fragments thereof (a) and (b)).

9 Claims, 7 Drawing Sheets

Specification includes a Sequence Listing.

(56) References Cited

U.S. PATENT DOCUMENTS

| | | | |
|---|---|---|---|
| 2008/0003239 | A1 | 1/2008 | Duke et al. |
| 2008/0274142 | A1 | 11/2008 | Monath et al. |
| 2009/0191240 | A1 | 7/2009 | Monath et al. |
| 2010/0047275 | A1 | 2/2010 | Stoloff et al. |
| 2010/0111996 | A1 | 5/2010 | Leclerc |
| 2010/0196411 | A1 | 8/2010 | Duke et al. |
| 2010/0303860 | A1 | 12/2010 | Stinchcomb et al. |
| 2011/0027314 | A1 | 2/2011 | Broeker et al. |
| 2012/0219575 | A1 | 8/2012 | Stoloff et al. |
| 2013/0034578 | A1 | 2/2013 | Rottier et al. |
| 2013/0129761 | A1 | 5/2013 | Garcia-Sastre et al. |
| 2013/0189306 | A1 | 7/2013 | Guirakhoo |
| 2013/0216575 | A1 | 8/2013 | Coller et al. |
| 2013/0243804 | A1 | 9/2013 | Stoloff et al. |
| 2014/0050759 | A1 | 2/2014 | Falkner et al. |
| 2014/0357845 | A1 | 12/2014 | Meijberg et al. |
| 2015/0024004 | A1 | 1/2015 | Monath et al. |
| 2015/0132331 | A1 | 5/2015 | Lu et al. |
| 2015/0174237 | A1 | 6/2015 | Mond et al. |
| 2015/0225474 | A1 | 8/2015 | Robinson et al. |
| 2015/0265695 | A1 | 9/2015 | Yao et al. |
| 2015/0273048 | A1 | 10/2015 | Kang et al. |
| 2016/0046697 | A1 | 2/2016 | Robinson et al. |
| 2016/0074502 | A1 | 3/2016 | Coller et al. |
| 2016/0129102 | A1 | 5/2016 | Stinchcomb et al. |
| 2016/0158340 | A1 | 6/2016 | Broeker et al. |
| 2016/0251413 | A1 | 9/2016 | Robinson et al. |
| 2016/0355553 | A1 | 12/2016 | Meijberg et al. |
| 2016/0362455 | A1 | 12/2016 | Meijberg et al. |
| 2016/0368950 | A1 | 12/2016 | Fischer et al. |
| 2017/0028053 | A1 | 2/2017 | Stoloff et al. |
| 2017/0121735 | A1 | 5/2017 | Falkner et al. |
| 2017/0158740 | A1 | 6/2017 | Tangy et al. |
| 2018/0002385 | A1 | 1/2018 | Garcia-Sastre et al. |
| 2018/0147277 | A1 | 5/2018 | Stoloff et al. |
| 2018/0185470 | A1 | 7/2018 | Stoloff et al. |
| 2019/0153074 | A1 | 5/2019 | Robinson et al. |
| 2019/0192649 | A1 | 6/2019 | Monath et al. |
| 2019/0201519 | A1 | 7/2019 | Stoloff et al. |
| 2019/0300578 | A1 | 10/2019 | Tangy et al. |
| 2019/0365883 | A1 | 12/2019 | Stoloff et al. |

FOREIGN PATENT DOCUMENTS

| | | | | |
|---|---|---|---|---|
| JP | 2001-046061 | A | | 2/2001 |
| JP | 2009-526028 | A | | 7/2009 |
| JP | 2010-268804 | A | | 12/2010 |
| JP | 2011-088864 | A | | 5/2011 |
| JP | 2011088864 | | * | 5/2011 |
| JP | 2013-075899 | A | | 4/2013 |
| JP | 2013-542224 | A | | 11/2013 |
| JP | 2014-506785 | A | | 3/2014 |
| JP | 2014-511119 | A | | 5/2014 |
| JP | 2015-502353 | A | | 1/2015 |
| JP | 2015-519348 | A | | 7/2015 |
| JP | 2015-524422 | A | | 8/2015 |
| JP | 2016-033151 | A | | 3/2016 |
| JP | 2017-019796 | A | | 1/2017 |
| JP | 2017-031225 | A | | 2/2017 |
| JP | 2017-512209 | A | | 5/2017 |
| JP | 2017-520252 | A | | 7/2017 |
| WO | WO2012060678 | | * | 5/2012 |
| WO | WO2015197565 | | * | 12/2015 |
| WO | WO-2016/109792 | A2 | | 7/2016 |

OTHER PUBLICATIONS

Martin et al., "The influence of Antigen Organization on B Cell responsiveness", Science, 1993, 262:1448-1451.*

Bachmann et al., "Neutralizing Antiviral B Cell Responses," Annu. Rev. Immunol., 1997, 15:235-270.

Bachmann et al., "T helper cell-independent neutralizing B cell response against vesicular stomatitis virus; role of antigen patterns in B cell induction?", Eur. J. Immunol., Dec. 1995, 25(12):3445-3451.

Bachmann et al., "The Influence of Antigen Organization on B Cell Responsiveness," Science, Nov. 26, 1993, 262(5138):1448-1451.

Cockburn et al., "Structurel insights into the neutralization mechanism of a higher primate antibody against dengue virus," The EMBO Journal, Feb. 1, 2012, 31:767-779.

Dai et al., "Structures of the Zika Virus Envelope Protein and Its Complex with a Flavivirus Broadly Protective Antibody," Cell Host & Microbe, May 11, 2016, 19:696-704.

De Alwis et al,. "Identification of human neutralizing antibodies that bind to complex epitopes on dengue virions," PNAS, May 8, 2012, 109(19):7439-7444.

Egorov et al., "The challenges of creating a universal influenza vaccine," Microbiology Independent Research Journal, Jul. 11, 2016, 3(1):31-41.

Ellebedy et al., "Induction of broadly cross-reactive antibody responses to the influenza HA stem region following H5N1 vaccination in humans," PNAS, Sep. 9, 2014, 111(36):13133-13138.

Hayward et al., "Natural T Cell-mediated Protection against Seasonal and Pandemic Influenza," American Journal of Respiratory and Critical Care Medicine, Jun. 15, 2015, 191(12):1422-1431.

Kanekiyo et al., "Self-assembling influenza nanoparticle vaccines elicit broadly neutralizing H1N1 antibodies," Nature, Jul. 4, 2013, 499(7456):102-106.

Krammer et al., "Chimeric Hemagglutinin Influenza Virus Vaccine Constructs Elicit Broadly Protective Stalk-Specific Antibodies," Journal of Virology, Jun. 2013, 87(12):6542-6550.

Lee et al., "Structural Characterization of Viral Epitopes Recognized by Broadly Cross-Reactive Antibodies," Curr. Top. Microbiol. Immunol., 2015, 386:323-341.

Lin et al., "Analysis of Epitopes on Dengue Virus Envelope Protein Recognized by Monoclonal Antibodies and Polyclonal Human Sera by a High Throughput Assay," PLOS Neglected Tropical Diseases, 2012, 6(1):e1447, 12 pages.

Mathew et al., "Elucidating the role of T cells in protection against and pathogenesis of dengue virus infections," Future Microbiology, 2014, 9(3):411-425.

Messer et al., "Dengue virus envelope protein domain I/II hinge determines long-lived serotype-specific dengue immunity," PNAS, Feb. 4, 2014, 111(5):1939-1944, and retraction published May 19, 2015, 112(20):E2738.

Noton et al., "Identification of the domains of the influenza A virus M1 matrix protein required for NP binding, oligomerization and incorporation into virions," Journal of General Virology, Aug. 2007, 88(8):2280-2290.

Okuno et al., "A Common Neutralizing Epitope Conserved between the Hemagglutinins of Influenza A Virus H1 and H2 Strains," Journal of Virology, May 1993, 67(5):2552-2558.

Rimmelzwaan et al., "Influenza virus CTL epitopes, remarkably conserved and remarkably variable," Vaccine, Oct. 23, 2009, 27(45):6363-6365.

Sagawa et al., "The immunological activity of a deletion mutant of influenza virus haemagglutinin lacking the globular region," Journal of General Virology, Jul. 1996, 77(7):1483-1487.

Steel et al., "Influenza Virus Vaccine Based on the Conserved Hemagglutinin Stalk Domain," mBio, May 18, 2010, 1(1):e00018-10, 9 pages.

Vamsee et al., "Influenza hemagglutinin stem-fragment immunogen elicits broadly neutralizing antibodies and confers heterologous protection," PNAS, Jun. 9, 2014, 111(25):E2514-2523.

Van de Sandt et al., "Differential Recognition of Influenza A Viruses by $M1_{58-66}$ Epitope-Specific $CD8^+$ T Cells is Determined by Extraepitopic Amino Acid Residues," Journal of Virology, Jan. 2016, 90(2):1009-1022.

Vratskikh et al., "Dissection of Antibody Specificities Induced by Yellow Fever Vaccination," PLOS Pathogens, 2013, 9(6):e1003458, 12 pages.

Wong et al., "Traditional and New Influenza Vaccines," Clinical Microbiology Reviews, Jul. 2013, 26(3):476-492.

Yassine et al., "Hemagglutinin-stem nanoparticles generate heterosubtypic influenza protection," Nature Medicine, Sep. 2015, 21(9):1065-1070.

(56) References Cited

OTHER PUBLICATIONS

Zhang et al., "Dissection of Influenza A Virus M1 Protein: pH-Dependent Oligomerization of N-Terminal Domain and Dimerization of C-Terminal Domain," PLOS One, May 24, 2012, 7(5):e37786, 12 pages.
Wu et al., "Characterization of immunity induced by M2e of influenza virus," Vaccine, Dec. 17, 2007, 25(52):8868-8873.

* cited by examiner

Fig. 1
influenza A virus universal vaccine antigen schematic diagram
1) HA-M1 fusion protein
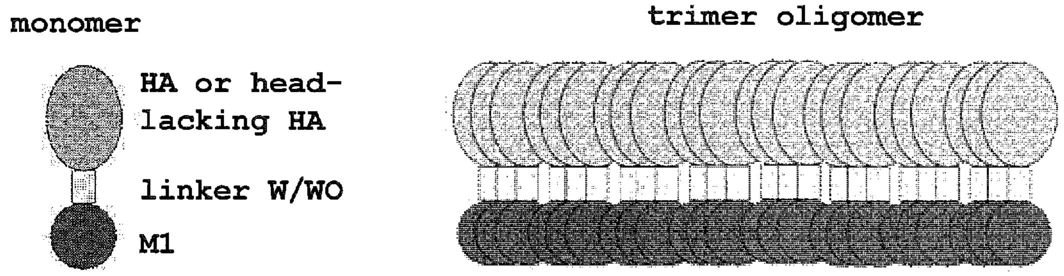
2) HA-M1 fusion protein and NP association
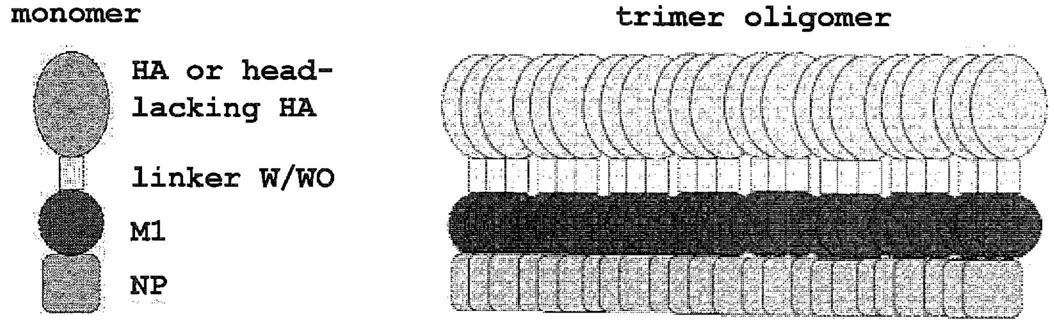

Fig. 2

HA Michigan strain (H1N1) (SEQ ID NO: 1)

```
  1 mkailvvlly tfttanadtl cigyhannst dtvdtvlekn vtvthsvnll edkhngklck
 61 lrgvaplhlg kcniagwilg npeceslsta sswsyivets nsdngtcypg dfinyeelre
121 qlssvssfer feifpktssw pnhdsnkgvt aacphagaks fyknliwlvk kgnsypklnq
181 syindkgkev lvlwgihhps ttadqqslyq nadayvfvgt sryskkfkpe iatrpkvrdq
241 egrmnyywtl vepgdkitfe atgnlvvpry aftmernags giiisdtpvh dcnttcqtpe
301 gaintslpfq nihpitigkc pkyvkstklr latglrnvps iqsrglfgai agfieggwtg
361 mvdgwygyhh qneqgsgyaa dlkstqnaid kitnkvnsvi ekmntqftav gkefnhlekr
421 ienlnkkvdd gfldiwtyna ellvllener tldyhdsnvk nlyekvrnql knnakeigng
481 cfefyhkcdn tcmesvkngt ydypkyseea klnrekidgv klestriyqi laiystvass
541 lvlvvslgai sfwmcsngsl qcrici
```

Matrix protein 1 (M1) Michigan strain (H1N1) (SEQ ID NO: 4)

```
  1 mslltevety vlsiipsgpl kaeiaqrles vfagkntdle almewlktrp ilspltkgil
 61 gfvftltvps erglqrrrfi qnalngngdp nnmdravkly kklkreitfh gakevslsys
121 tgalascmgl iynrmgtvtt eaafglvcat ceqiadsqhr shrqmatttn plirhenrmv
181 lasttakame qvagsseqaa eamevanktr qmvhamrtig thpsssaglr ddllenlqay
241 qkrmgvqmqr fk
```

Nucleocapsid protein Michigan strain (H1N1) (SEQ ID NO: 6)

```
  1 masqgtkrsy eqmetggerq dtteirasvg rmiggigrfy iqmctelkls dydgrliqns
 61 itiermvlsa fderrnkyle ehpsagkdpk ktggpiyrri dgkwtrelil ydkeeirrvw
121 rqanngedat aglthimiwh snlndatyqr tralvrtgmd prmcslmqgs tlprrsgaag
181 aavkgvgtia melirmikrg indrnfwrge ngrrtrvaye rmcnilkgkf qtaaqrammd
241 qvresrnpgn aeiedlifla rsalilrgsv ahksclpacv yglavasghd feregyslvg
301 idpfkllqns qvvslmrpne npahksqlvw machsaafed lrvssfirgk kviprgklst
361 rgvqiasnen vetmdsntle lrsrywairt rsggntnqqk asagqisvqp tfsvqrnlpf
421 eratvmaafs gnnegrtsdm rtevirmmes akpedlsfqg rgvfelsdek atnpivpsfd
481 msnegsyffg dnaeeydn
```

Fig. 3

HA-M1 fusion polypeptide (SEQ ID NO: 8)

```
  1 dtlcigyhan nstdtvdtvl eknvtvthsv nlledkhngk lcklrgvapl hlgkcniagw
 61 ilgnpecesl stasswsyiv etsnsdngtc ypgdfinyee lreqlssvss ferfeifpkt
121 sswpnhdsnk gvtaacphag aksfyknliw lvkkgnsypk lnqsyindkg kevlvlwgih
181 hpsttadqqs lyqnadayvf vgtsryskkf kpeiatrpkv rdqegrmnyy wtlvepgdki
241 tfeatgnlvv pryaftmern agsgiiisdt pvhdcnttcq tpegaintsl pfqnihpiti
301 gkcpkyvkst klrlatglrn vpsiqsrglf gaiagfiegg wtgmvdgwyg yhhqneqgsg
361 yaadlkstqn aidkitnkvn sviekmntqf tavgkefnhl ekrienlnkk vddgfldiwt
421 ynaellvlle nertldyhds nvknlyekvr nqlknnakei gngcfefyhk cdntcmesvk
481 ngtydypkys eeaklnreki dgvklestri ycsngslqcr icimslltev etyvlsiips
541 gplkaeiaqr lesvfagknt dlealmewlk trpilspltk gilgfvftlt vpserglqrr
601 rfiqnalngn gdpnnmdrav klykklkrei tfhgakevsl systgalasc mgliynrmgt
621 vtteaafglv catceqiads qhrshrqmat ttnplirhen rmvlasttak ameqvagsse
681 qaaeamevan ktrqmvhamr tigthpsssa glrddllenl qayqkrmgvq mqrfk
```

head-lacking HA-M1 fusion polypeptide (SEQ ID NO: 9)

```
  1 dtlcigyhan nstdtvdtvl eknvtvthsv nlledkhngk lcklrgvapl hlgkcniafq
 61 nihpitigkc pkyvkstklr latglrnvps iqsrglfgai agfieggwtg mvdgwygyhh
121 qneqgsgyaa dlkstqnaid kitnkvnsvi ekmntqftav gkefnhlekr ienlnkkvdd
181 gfldiwtyna ellvllener tldyhdsnvk nlyekvrnql knnakeigng cfefyhkcdn
241 tcmesvkngt ydypkyseea klnrekidgv klestriycs ngslqcrici mslltevety
301 vlsiipsgpl kaeiaqrles vfagkntdle almewlktrp ilspltkgil gfvftltvps
361 erglqrrrfi qnalngngdp nnmdravkly kklkreitfh gakevslsys tgalascmgl
421 iynrmgtvtt eaafglvcat ceqiadsqhr shrqmatttn plirhenrmv lasttakame
481 qvagsseqaa eamevanktr qmvhamrtig thpsssaglr ddllenlqay qkrmgvqmqr
541 fk
```

molecular weight of head-lacking HA-M1 fusion protein

CROSS-IMMUNIZING ANTIGEN VACCINE AND METHOD FOR PREPARATION THEREOF

CROSS-REFERENCE TO RELATED APPLICATIONS

This application is the U.S. National Stage of PCT/JP2018/047379, filed Dec. 21, 2018, which claims priority to JP 2017-245606, filed Dec. 21, 2017.

The instant application contains a Sequence Listing which has been submitted in ASCII format via EFS-WEB and is hereby incorporated by reference in its entirety. Said ASCII copy, created on Jun. 17, 2020, is named sequence.txt and is 34,902 bytes.

TECHNICAL FIELD

The present invention relates to a fusion polypeptide that induces immune response to a virus, a multimer of the fusion polypeptide, pharmaceutical use of the fusion polypeptide and a multimer thereof, a production method of the multimer and the like.

BACKGROUND ART

Various vaccines have been developed against viruses that repeat antigen mutations and viruses having multiple subtypes of serotype. For example, in the case of influenza virus, the HA antigen present in the outer veil of influenza virus particles is marketed as a seasonal influenza A virus HA split vaccine. In the influenza virus HA gene, genetic exchange occurs among subtypes A, and antigen mutations occur due to mutations in the base sequence, and mutations concentrate at the head of the three-dimensional structure of the HA protein. Since the head of HA is the major epitope for neutralizing antibody, the marketed HA split vaccines and virus inactivated vaccines have little effect on new mutant strains. On the other hand, the stem region has few mutations but has not been used as a subtype A vaccine antigen due to its low immunogenicity. Okuno et al., Research Institute for Microbial Diseases, Osaka University, reported for the first time in 1993 that an anti-stem antibody that can cross-react with and neutralize influenza virus A1 and A2 type strains was induced (non-patent document 1). The same group also reported in 1996 that an anti-stem antibody capable of neutralizing type 1 and type 2 was induced in animals immunized with HA deficient in the head region of HA gene (non-patent document 2). Since then, universal vaccines using stem antigens have been developed around the world (non-patent documents 3, 4, 5, 6). On the other hand, monomeric (monomer) antigen proteins have low immunogenicity, and therefore, HA split vaccines have a weak effect. M. F. Bachmann et al. analyzed the relationship between immunogenicity and antigen structure, and reported that highly organized (multimerized, oligomerized) antigens have high immunogenicity and can induce memory B cells, and thus it is important to organize vaccine antigen (non-patent documents 7, 8, 9). It has been reported that the fusion protein of HA and ferritin enhances the immunogenicity of HA by forming a multimer by oligomerization activity of ferritin (non-patent documents 10, 11). The host immune response with influenza virus HA split vaccine and inactivated vaccine is mainly humoral immunity that neutralizes virus by induction of antibodies against HA antigens. On the other hand, another immune response that destroys infected cells and suppresses the spread of viral infection is cellular immunity. Influenza virus vaccines that are commercially available at present hardly show cellular immunity inducibility. Influenza virus antigen (CTL epitope) that binds to major histocompatibility complex class 1 molecule of infected cells and is recognized by the T cell receptor of cytotoxic T cell (CTL) is reported to be present in matrix (M1) protein and nucleocapsid (NP) protein (non-patent documents 12, 13, 14). Since the amino acid sequence of the matrix (M1) protein and nucleocapsid (NP) protein is conserved between the A subtypes, cross-cell immunity is established between the A subtypes. M1 protein has the ability to form a polymer (oligomer) and binds to NP (non-patent documents 15, 16). Refer to non-patent documents 17, 18 for the development status of influenza A virus vaccine.

On the other hand, in the case of dengue virus, there are four serotype subtypes D1, D2, D3 and D4. When a patient infected with one type and having antibody induced is infected with other type, the antibody enhances virus growth of secondary infection and severe dengue hemorrhagic fever and dengue shock syndrome are caused (non-patent documents 19, 20). Therefore, a simple inactivated tetravalent vaccine or a tetravalent virus particle surface protein envelope antigen vaccine for D1, 2, 3, or 4 has not been developed due to such risk.

Various vaccines for influenza virus and dengue virus have been reported (patent documents 1-8).

As described above, it is difficult to predict an epidemic of a virus that repeats antigen mutations and a virus having multiple subtypes of serotype, and therefore, a sufficiently effective vaccine that covers variant viruses and viruses of various serotypes has not been developed. There is a need for the development of antiviral vaccines that confer cross immunity effective against mutant viruses and a wide range of subtypes of serotype.

DOCUMENT LIST

Patent Documents patent document 1: JP-A-2017-19796
patent document 2: JP-A-2017-31225
patent document 3: JP-A-2001-46061
patent document 4: JP-A-2010-268804
patent document 5: National Publication of International Patent Application No. 2013-542224
patent document 6: National Publication of International Patent Application No. 2015-524422
patent document 7: JP-A-2016-33151
patent document 8: National Publication of International Patent Application No. 2017-520252

Non-Patent Documents non-patent document 1: Y. Okuno et al, A common neutralizing epitope conserved between the hemagglutinins of Influenza A virus H1 and H2 strains J. Virol, 67, 2552-2558(1993) non-patent document 2: H. Sagawa et al, The immunological activity of a deletion mutant of influenza virus haemagglutinin lacking the globular region. J. Gen. Virol, 77, 1483-1487(1996) non-patent document 3: J. Steel et al, Influenza virus vaccine based on conserved hemagglutinin stalk domain. mBio, 1, 1-9(2010)
non-patent document 4: F. Krammer et al, Chimeric hemagglutinin influenza virus Vaccine constructs elicit broadly protective stalk-specific antibodies. J. Virol, 87, 6542-6550(2013)

non-patent document 5: V. V. A. Mallajosyula et al, Influenza hemagglutinin stem-fragment immunogen elicites broadly neutralizing antibodies and confers heterologous protection. PNAS, E2514-E2523(2014)
non-patent document 6: A. H. Ellebedy et al, Induction of broadly cross-reactive antibody responses to the influenza HA stem region following H5N1 vaccination in humans. PNAS, 111, 13133-13138(2014)
non-patent document 7: M. F. Bachmann et al, The influence of antigen organization on B cell responsiveness. Science, 262, 1448-1451(1993)
non-patent document 8: M. F. Bachmann et al, T helper cell-independent neutralizing B cell response against vesicular stomatitis virus: role of antigen patterns in B cell induction? Eur. J. Immunol, 25, 3445-3451(1995)
non-patent document 9: M. F. Bachmann and R. M. Zinkernagel, Neutralizing antiviral B cell responses. Ann, Rev. Immunol, 15, 235-270(1997)
non-patent document 10: M. Kanekiyo et al, Self-assembling influenza nanoparticle vaccines elicit broadly neutralizing H1N1 antibodies. Nature, 499, 102-108(2013)
non-patent document 11: H. M. Yassine et al, Hemagglutinin-stem nanoparticles generate heterosubtypic influenza protection. Nature Medicine, online publication, doi:10. 1038/nm. 3927(2015)
non-patent document 12: A. C. Hayward et al, Natural cell-mediated protection against seasonal and pandemic influenza, American J. Respiratory and Critical Care Medicine, 191, 1422-1431(2015)
non-patent document 13: G. F. Rimmelzwaan, J. H. C. M Kreijtz, R. Bodewes, R. A. M Fouchier and A. D. M. E Osterhaus, Influenza virus CTL epitopes, remarkably conserved and remarkably variable. Vaccine, 27, 6363-6365 (2009)
non-patent document 14: C. E. van de Sandt et al, Differential recognition of influenza A virus by M158-66 epitope-specific CD8+ T cells is determinant by extra-epitopic amino acid residues. J. Virol, 90, 1009-1022 (2016)
non-patent document 15: S. L. Noton et al, Identification of the domains of the influenza A virus M1 matrix protein required for NP binding, oligomerization and incorporation into virions. J. Gen. Virol, 88, 2280-2290(2007)
non-patent document 16: K. Zhang et al, Dissection of influenza A virus M1 protein: pH-dependent oligomerization of N-terminal domain and dimerization of C-terminal domain. PLOS ONE, 7, e37786, 1-12(2012)
non-patent document 17: S-S Wong and R. J. Webby, Traditional and new influenza vaccines. Clinical Microbiology Reviews 26, 476-492 (2013)
non-patent document 18: A. Y. Egorov. The challenges of creating a universal influenza vaccine. MIR J., 5, 32-41 (2016)
non-patent document 19: J. Cockburn et al, Structural insights into the neutralization mechanism of a higher primate antibody against dengue virus. EMBO J, 31, 767-779(2012)
non-patent document 20: H-E. Lin et al, Analysis of epitopes on dengue virus envelope protein recognized by monoclonal antibodies and polyclonal human sera by a high throughput assay. PLOS Neglected Tropical Diseases, 6, e1447, 1-12(2012)
non-patent document 21: R. de Alwis et al, Identification of human neutralizing antibodies that bind to complex epitopes on dengue virions. PNAS, 109, 7439-7444(2012)
non-patent document 22: O. Vratskikh, et al, Dissection of antibody specificities induced by yellow fever vaccination. PLOS Pathogens, 9, e1003458, 1-12(2013)
non-patent document 23: W. B. Messer, et al, Dengue virus envelope protein domain I/II hinge determines long-lived serotype-specific dengue immunity. PNAS, 111, 1939-1944(2014)
non-patent document 24: L. Dai, et al, Structure of the Zika virus envelope protein and its complex with a flavivirus broadly protective antibody. Cell Host & Microbe, 19, 1-9(2016)
non-patent document 25: A. Mathew, et al, Elucidating the role of T cells in protection against and pathogenesis of dengue virus infections. Future Microbiol. 9, 411-425 (2014)
non-patent document 26: P. S. Lee and I. A. Wilson, Structural characterization of viral epitopes recognized by broadly cross-reactive antibodies. Curr. Top. Microbiol. Immunol. 386, 323-341(2015)

SUMMARY OF THE INVENTION

Problems to be Solved by the Invention

The present invention aims to provide an antivirus vaccine that effectively imparts cross immunity to a variant virus and a wide range of subtypes.

Means of Solving the Problems

The present inventors have conducted intensive studies and found that a humoral immune response (antibody production) and a cellular immune response (cytotoxic T cell proliferation) can be effectively induced against viruses of a broad range of subtypes by administering, as a vaccine to a mammal, a fusion polypeptide multimer comprising a viral antigen or a fragment thereof containing a B cell epitope conserved among subtypes (hereinafter, “B cell epitope conserved among subtypes” is sometimes to be referred to as “conserved B cell epitope”, and “antigen containing B cell epitope conserved among subtypes” is sometimes to be referred to as “conserved B cell epitope-containing antigen”, and the like), and an antigen or a fragment thereof containing a T cell epitope conserved among subtypes (hereinafter “T cell epitope conserved among subtypes” is sometimes to be referred to as “conserved T cell epitope”, and “antigen containing T cell epitope conserved among subtypes” is sometimes to be referred to as “conserved T cell epitope-containing antigen” and the like), and obtained by oligomerizing the resulting fusion polypeptide having an oligomerization activity.

Influenza virus contains, in the stem region of HA, a B cell epitope that induces neutralizing antibody highly conserved among subtypes. Thus, HA or a fragment of HA containing the conserved B cell epitope (e.g., a fragment consisting of stem region of HA, head region-deficient HA in which “head region” frequently showing mutation is deleted from HA, a fragment comprising the conserved B cell epitope) can be used as a conserved B cell epitope-containing antigen or a fragment thereof. Also, a cytotoxic T cell epitope highly conserved among subtypes is included within matrix protein 1 (M1). Thus, M1 or M1 fragment containing the conserved T cell epitope (e.g., a fragment comprising the conserved T cell epitope) can be used as a conserved T cell epitope-containing antigen. M1 has an oligomerization activity. Thus, using M1 or a fragment thereof having an oligomerization activity as an antigen containing T cell epitope conserved among subtypes or a fragment thereof containing a T cell epitope conserved among subtypes, the fusion polypeptide has an oligomerization activity and a multimer thereof is easily formed by the oligomerization activity. In addition, nucleocapsid protein (NP) also contains cytotoxic T cell epitope highly conserved among subtypes. Thus, NP or an NP fragment containing the conserved T cell epitope (e.g., a fragment comprising the conserved T cell epitope) can be used as a conserved T cell epitope-containing antigen or a fragment thereof. Since NP can associate with M1, NP may be associated with M1 antigen residue in the fusion protein without being incorporated into the fusion protein.

Dengue virus contains, in the DI and DII domains of E protein, a B cell epitope that induces neutralizing antibody highly conserved among subtypes. Thus, E protein, or E protein fragment containing DI and DII domains (e.g., a fragment consisting of DI and DII domains) can be used as a conserved B cell epitope-containing antigen or a fragment thereof. Also, a cytotoxic T cell epitope highly conserved among subtypes is included within dengue virus N3. Thus, N3 or a fragment of N3 containing the conserved T cell epitope (e.g., a fragment comprising the conserved T cell epitope) can be used as a conserved CTL epitope-containing antigen residue (non-patent document 25). By incorporating a polypeptide having an oligomerization activity such as matrix protein (M1) into the fusion polypeptide, the fusion polypeptide exhibits an oligomerization activity and easily forms a multimer.

The present inventors have further studied based on the above-mentioned finding, which resulted in the completion of the present invention.

That is, the present invention provides the following.

[1] A fusion polypeptide that induces a humoral immune response and a cellular immune response to a virus, comprising antigens or fragments thereof of the following (a) and (b), and having an oligomerization activity:

(a) an antigen of the virus or a fragment thereof containing a B cell epitope conserved among subtypes of the virus; and (b) an antigen of the virus or a fragment thereof containing a T cell epitope conserved among subtypes of the virus (wherein the antigen(s) or the fragment(s) thereof of (a) and/or (b) have an oligomerization activity, or the fusion polypeptide further comprises (c) a polypeptide having an oligomerization activity in addition to the antigens or the fragments thereof (a) and (b)).

[2] The fusion polypeptide according to [1] wherein the virus is an influenza A virus.

[3] The fusion polypeptide according to [2] wherein the antigen or the fragment thereof of (a) is hemagglutinin or a fragment thereof.

[4] The fusion polypeptide according to [3] wherein the antigen or the fragment thereof of (a) is head-lacking hemagglutinin.

[5] The fusion polypeptide according to [3] or [4] comprising a partial sequence consisting of Gln 310-Asp 390 of the amino acid sequence shown in SEQ ID NO: 1.

[6] The fusion polypeptide according to any one of [2] to [5] wherein the antigen or the fragment thereof of (b) is a matrix protein 1 or a fragment thereof.

[7] The fusion polypeptide according to [6] wherein the antigen or the fragment thereof of (b) has an oligomerization activity.

[8] The fusion polypeptide according to [6] or [7] wherein the T cell epitope comprises the amino acid sequence shown in SEQ ID NO: 3.

[9] A complex comprising the fusion polypeptide according to any one of [6] to [8] and a nucleocapsid.

[10] The fusion polypeptide according to [1] wherein the virus is a dengue virus.

[11] The fusion polypeptide according to [10] wherein the antigen or the fragment thereof of (a) is an E protein or a fragment thereof.

[12] The fusion polypeptide according to [11] wherein the antigen or the fragment thereof of (a) comprises DI and DII domains of E protein.

[13] The fusion polypeptide according to any one of [10] to [12] wherein the antigen or the fragment thereof of (b) is NS3 or a fragment thereof.

[14] The fusion polypeptide according to any one of [10] to [13] comprising matrix protein 1 or a fragment thereof having an oligomerization activity in addition to the antigens or fragments thereof of (a) and (b).

[15] A multimer of the fusion polypeptide according to any one of [1] to [8] and [10] to [14], or the complex according to [9] that can be formed by oligomerization of the fusion polypeptide or the complex.

[16] A pharmaceutical composition comprising the fusion polypeptide according to any one of [1] to [8] and [10] to [14], the complex according to [9], or the multimer according to [15].

[17] The pharmaceutical composition according to [16] that is for inducing an immune response to the virus.

[18] The pharmaceutical composition according to [16] that is for the prophylaxis or treatment of infection with the virus.

[19] A method for inducing an immune response to a virus in a mammal comprising administering an effective amount of the fusion polypeptide according to any one of [1] to [8] and [10] to [14], the complex according to [9], or the multimer according to [15] to the mammal.

[20] A method for prophylaxis or treatment of an infection with a virus in a mammal comprising administering an effective amount of the fusion polypeptide according to any one of [1] to [8] and [10] to [14], the complex according to [9], or the multimer according to [15] to the mammal.

[21] The fusion polypeptide according to any one of [1] to [8] and [10] to [14], the complex according to [9], or the multimer according to [15] for use in inducing an immune response to the virus.

[22] The fusion polypeptide according to any one of [1] to [8] and [10] to [14], the complex according to [9], or the multimer according to [15] for use in prophylaxis or treatment of an infection with the virus.

[23] A method for producing a pharmaceutical composition for inducement of an immune response to a virus or prophylaxis or treatment of an infection with the virus comprising oligomerizing the fusion polypeptide according to any one of [1] to [8] and [10] to [14], or the complex according to [9] to give a multimer of the fusion polypeptide or the complex.

Effect of the Invention

The present invention provides an antivirus vaccine that imparts cross immunity effective for a variant virus and a wide range of subtypes. According to the present invention, an effective vaccine that cross-reacts with a wide range of influenza A viruses including seasonal influenza virus and predictable highly pathogenic pandemic influenza viruses is expected to be provided.

BRIEF DESCRIPTION OF THE DRAWINGS

FIG. 1 is a schematic showing of influenza A virus vaccine antigen fusion polypeptide (HA-M1 fusion polypeptide, HA-MI fusion polypeptide associated with NP).

FIG. 2 shows the amino acid sequences of HA antigen, M1 antigen and NP antigen of influenza A virus Michigan strain (H1N1).

FIG. 3 shows an example of the amino acid sequence of influenza A virus vaccine antigen fusion polypeptide (HA-M1 fusion polypeptide, head-lacking HA-M1 fusion polypeptide).

DESCRIPTION OF EMBODIMENTS

1. Polypeptide

Figure 4:
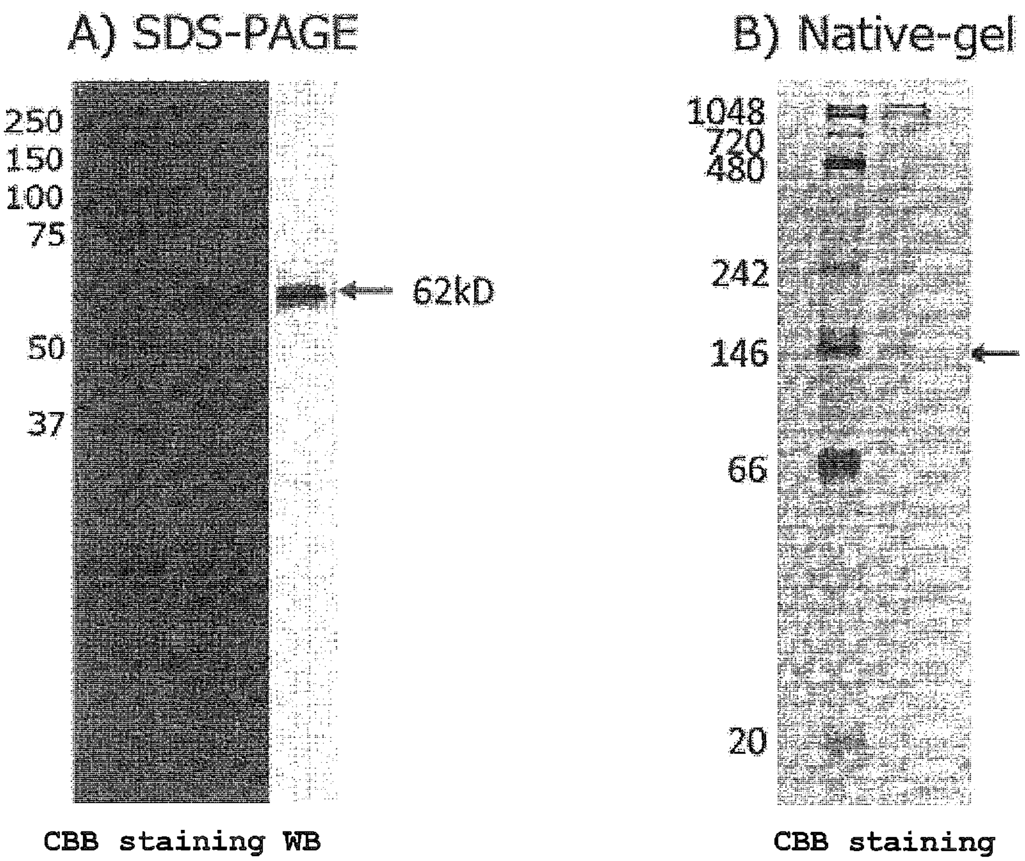
FIG. 4 shows the results of SDS-PAGE(A) and Native-PAGE(B) of influenza A virus vaccine antigen fusion polypeptide (head-lacking HA-M1 fusion protein (+GS linker+6×His Tag)) expressed in a wheat cell-free system.

The present invention provides a fusion polypeptide that induces a humoral immune response and a cellular immune response to a virus, comprising antigens or fragments thereof of the following (a) and (b) and having an oligomerization activity:

(a) an antigen of the virus or a fragment thereof containing a B cell epitope conserved among subtypes of the virus; and (b) an antigen of the virus or a fragment thereof containing a T cell epitope conserved among subtypes of the virus (wherein the antigen(s) or fragment(s) thereof of (a) and/or (b) have an oligomerization activity, or the fusion polypeptide further comprises (c) a polypeptide having an oligomerization activity in addition to the antigens or fragments thereof of (a) and (b)).

Examples of the virus to which the present invention is applied include, but are not limited to, viruses belonging to Orthomyxoviridae, Flaviviridae, Herpesviridae, Adenoviridae, Papillomaviridae, Polyomaviridae, Poxviridae, Reoviridae, Coronaviridae, Picornaviridae, Togaviridae, Caliciviridae, Astroviridae, Paramyxoviridae, Rhabdoviridae; Filoviridae, Arenaviridae, Bunyaviridae, Retroviridae and the like. Preferred virus to which the present invention is applied is a virus belonging to Orthomyxoviridae, or a virus belonging to Flaviviridae. Examples of the virus belonging to Orthomyxoviridae include, but are not limited to, influenza virus (Type A, Type B, Type C) and the like, and preferred is influenza A virus. Examples of the virus belonging to Flaviviridae include, but are not limited to, dengue virus, Japanese encephalitis virus, yellow fever virus, West Nile fever virus and the like, and preferred is dengue virus. In a preferable embodiment, a virus to which the present invention is applied is influenza A virus or dengue virus.

A humoral immune response to a virus means induction of antibody production against the virus. The antibody can be a neutralizing antibody. The neutralizing antibody binds to a viral antigen, inhibits infection and proliferation of the virus, or promotes elimination of the virus to the outside of the body. Cellular immune response to a virus means proliferation of a cytotoxic T cell (CTL) that kills virus-infected cells. Cytotoxic T cell recognizes the virus antigen-derived peptide presented to the major histocompatibility antigen class 1 molecule by T cell receptor and destroys the virus-infected cells presented with the peptide, whereby expansion of virus infection is suppressed. The fusion polypeptide of the present invention contains (a) an antigen of a virus or a fragment thereof containing a B cell epitope conserved among subtypes of the virus (conserved B cell epitope-containing antigen or a fragment thereof); and (b) an antigen of a virus or a fragment thereof containing a T cell epitope conserved among subtypes of the virus (conserved T cell epitope-containing antigen or a fragment thereof), due to which it has an activity to induce a humoral immune response and cellular immune response to the virus.

In the present invention, the B cell epitope refers to a particular structural unit of a virus antigen which is induced in a host mammal infected with the virus and which an antibody (preferably neutralizing antibody) to the virus antigen recognizes and binds to. In the present invention, a B cell epitope conserved among subtypes of a virus is used. That is, the B cell epitope used in the present invention maintains an amino acid sequence or three-dimensional structure in at least two (for example, 3 or more, 4 or more, 5 or more, 6 or more, 7 or more, or 8 or more) subtypes of a specific virus and does not contain mutation. Using the thus-conserved B cell epitope, a humoral immune reaction (antibody production) can be induced by cross-reaction against viruses that repeat antigenic mutations or viruses that have multiple subtypes of serotype. With respect to respective viruses, various virus antigens containing B cell epitope conserved among subtypes have been studied and can be used for the present invention. For example, for influenza A virus, hemagglutinin (HA) can be used as a virus antigen containing B cell epitope conserved among subtypes. For dengue virus, an envelope protein (E protein) can be used as a virus antigen containing B cell epitope conserved among subtypes.

In the HA gene of influenza A virus, genetic exchange occurs among subtypes, and antigen mutations occur due to mutations in the base sequence, and the mutations concentrate at the head of the three-dimensional structure of HA. On the other hand, the stem region has less mutations and the amino acid sequence is conserved among the subtypes, and the common epitope for the A subtype HA stem region is considered to be a three-dimensional structure including a membrane fusion domain (non-patent document 26). It has been reported that the three-dimensional structural epitope within this stem region is conserved among influenza A virus subtypes and induces an antibody that can cross-react and neutralize among the subtypes (non-patent document 26). HA of influenza A virus can be phylogenetically classified into group 1 (H1, H2, H5, H6, H8, H9, H11, H12, H13, H16, H17, and H18) and group 2 (H3, H4, H7, H10, H14, and H15), and the three-dimensional structural epitope within the stem region is conserved particularly well in each of these groups (non-patent document 26).

One embodiment of the HA amino acid sequence of influenza A virus (HA Michigan strain (H1N1)) is shown in FIG. 2 and SEQ ID NO: 1.

Met 1-Ala 17 of SEQ ID NO: 1 is signal peptide region.

Asp 18-Arg 344 of SEQ ID NO: 1 is H1 region.

Gly 76-Gln 308 of SEQ ID NO: 1 is head region in the H1 region.

Gly 345-Tyr 528 of SEQ ID NO: 1 is H2 region.

Gly 345-Val 399 of SEQ ID NO: 1 is membrane fusion region in the H2 region.

Gln 529-Met 554 of SEQ ID NO: 1 is transmembrane region.

Cys 555-Ile 566 of SEQ ID NO: 1 is cytoplasm region.

The sequence obtained by removing the signal peptide region (Met 1-Ala 17) from SEQ ID NO: 1 corresponds to the amino acid sequence of a mature type of HA of influenza A virus.

The HA amino acid sequence of influenza A virus may vary among subtypes and strains due to mutation. Even if it is influenza A virus HA having an amino acid sequence different from SEQ ID NO: 1, those who have ordinary skills in the art can easily identify a signal peptide region as a region corresponding to Met 1-Ala 17 of SEQ ID NO: 1, H1 region as a region corresponding to Asp 18-Arg 344 of SEQ ID NO: 1, head region as a region corresponding to Gly 76-Gln 308 of SEQ ID NO: 1, H2 region as a region corresponding to Gly 345-Tyr 528 of SEQ ID NO: 1, membrane fusion region as a region corresponding to Gly 345-Val 399 of SEQ ID NO: 1, transmembrane region as a region corresponding to Gln 529-Met 554 of SEQ ID NO: 1, and cytoplasm region as a region corresponding to Cys 555-Ile 566 of SEQ ID NO: 1, based on the above-mentioned description and by performing alignment with SEQ ID NO:

Gln 310-Asp 390 of SEQ ID NO: 1 is the stem region. B cell three-dimensional structural epitope which is conserved between influenza virus Type A1 strain and Type A3 strain, or conserved among influenza A virus subtypes having any of HAs (H1, H2, H5, H6, H8, H9, H11, H12, H13, H16, H17, and H18) of group 1, is located within Gln 310-Asp 390 (stem region) of SEQ ID NO: 1. Even if it is influenza A virus HA having an amino acid sequence different from SEQ ID NO: 1, those who have ordinary skills in the art can easily identify a stem region as a region corresponding to Gln 310-Asp 390 of SEQ ID NO: 1.

When B cell epitope conserved among subtypes is present, it is possible to induce a humoral immune response (antibody production) that cross-reacts with the viruses of the subtypes. Thus, HA fragment containing B cell epitope (e.g., epitope with three-dimensional structure in stem region) conserved among subtypes of influenza A virus can be used in the present invention. When an HA fragment of influenza A virus is used which contains epitope with three-dimensional structure in stem region, the length of the fragment is not particularly limited as long as it induces an antibody that recognizes and binds to the three-dimensional structural epitope in the stem region. For example, it is not more than 500 amino acids, not more than 400 amino acids, not more than 300 amino acids, not more than 200 amino acids, not more than 100 amino acids, not more than 90 amino acids, not more than 80 amino acids, not more than 70 amino acids, not more than 60 amino acids, not more than 50 amino acids, not more than 40 amino acids, not more than 30 amino acids, not more than 20 amino acids, not more than 15 amino acids, or not more than 10 amino acids. As the HA fragment containing three-dimensional structural epitope in the stem region, a polypeptide consisting of a partial sequence of the amino acid sequence shown in SEQ ID NO: 1 and containing Gln 310-Asp 390 of the amino acid sequence shown in SEQ ID NO: 1 can be mentioned. The length of the partial sequence is not particularly limited as long as it induces an antibody that recognizes and binds to the three-dimensional structural epitope in the stem region. For example, it is not more than 500 amino acids, not more than 400 amino acids, not more than 300 amino acids, not more than 200 amino acids, not more than 100 amino acids, not more than 90 amino acids, or not more than 80 amino acids. A polypeptide consisting of the stem region of HA of influenza A virus (e.g., polypeptide consisting of Gln 310-Asp 390 of the amino acid sequence shown in SEQ ID NO: 1) can also be used in the present invention. As mentioned above, the mutations in the HA gene of influenza virus are concentrated in the head region. Thus, in a preferable embodiment, HA fragment containing B cell epitope conserved among subtypes of influenza A virus (e.g., epitope with three-dimensional structure in the stem region) does not contain all or a part of the head region. As an HA fragment that contains B cell epitope conserved among subtypes (e.g., epitope with three-dimensional structure in stem region) of influenza A virus and does not contain all or a part of the head region, a polypeptide consisting of the stem region can be mentioned. A head-lacking HA in which head region is deleted from full-length HA, and a fragment thereof containing the three-dimensional structural epitope in the stem region can also be used in the present invention as preferred HA fragments. An example of the amino acid sequence of the head-lacking HA is shown in SEQ ID NO: 2. The sequence obtained by removing the signal peptide region (Met 1-Ala 17) from SEQ ID NO: 2 corresponds to the amino acid sequence of head-lacking HA of mature influenza A virus.

Dengue virus contains, in the DI and DII domains of E protein, a B cell epitope that induces neutralizing antibody highly conserved among subtypes. Thus, E protein, or E protein fragment containing DI and DII domains (e.g., a fragment consisting of DI and DII domains) can be used as a virus antigen or a fragment thereof containing B cell epitope conserved among subtypes (non-patent documents 21, 22, 23, and 24).

The size of the conserved B cell epitope-containing antigen or a fragment thereof is not particularly limited and it is generally not more than 2000 amino acids (e.g., not more than 1000 amino acids, not more than 750 amino acids, not more than 600 amino acids, not more than 500 amino acids, not more than 400 amino acids, or not more than 300 amino acids).

In the present invention, the T cell epitope refers to a particular structural unit of a virus antigen which is induced in a host mammal infected with the virus and which T cell receptor on cytotoxic T cell surface recognizes and binds to. Cytotoxic T cell recognizes a T cell epitope-containing peptide (or peptide consisting of T cell epitope) presented on the major histocompatibility antigen class 1 molecule by T cell receptor and destroys the virus-infected cells presenting the peptide. In the present invention, a T cell epitope conserved among subtypes of a virus is used. That is, the T cell epitope used in the present invention maintains an amino acid sequence in at least two (for example, 3 or more, 4 or more, 5 or more, 6 or more, 7 or more, or 8 or more) subtypes of a specific virus and does not contain mutation. Using the thus-conserved T cell epitope, a cellular immune response (CTL proliferation) can be induced by cross-reaction against viruses that repeat antigenic mutations or viruses that have multiple subtypes of serotype. With respect to respective viruses, various virus antigens containing T cell epitope conserved among subtypes have been studied and can be used for the present invention. For example, for influenza A virus, matrix protein 1 (M1) and nucleocapsid (NP) can be used as virus antigens containing T cell epitope conserved among subtypes. For dengue virus, NS3 can be used as a virus antigen containing T cell epitope conserved among subtypes.

T cell epitope that binds to major histocompatibility complex class 1 molecule of infected cells and is recognized by the T cell receptor of cytotoxic T cell (CTL) is reported to be present in M1 and NP of influenza A virus (non-patent documents 12, 13, and 14). Since M1 and NP have amino acid sequences conserved among subtypes of influenza A virus, cross reacted cellular immunity is established between the subtypes. Representative amino acid sequences of M1 and NP of influenza A virus are respectively shown in FIG. 2, SEQ ID NO: 4 and SEQ ID NO: 6. The sequence of the conserved T cell epitope of M1 of MINI and H3N2 of influenza A virus is, for example, gilgfvftl (SEQ ID NO: 3) and is located at 58-66 of the full-length amino acid sequence of M1 (SEQ ID NO: 4) (non-patent document 14). The sequence of the conserved T cell epitope of NP of H1N2 and H3N2 of influenza A virus is, for example, srywairtr (SEQ ID NO: 5) and is located at 383-391 of the full-length amino acid sequence of NP (SEQ ID NO: 6) (non-patent document 13). However, since the genotypes of major histocompatibility antigen HLA, which is a human antigen presenting molecule, are diverse, the T cell epitope peptide sequence that binds to HLA is not limited to the above-mentioned sequences.

When T cell epitope conserved among subtypes is present, it is possible to induce a cellular immune response (CTL proliferation) that cross-reacts with the viruses of the subtypes. Thus, M1 or NP fragment containing conserved T cell epitope of influenza A virus can be used in the present invention. As the M1 fragment containing conserved T cell epitope, a polypeptide containing the amino acid sequence shown in SEQ ID NO: 3, and a partial sequence of the amino acid sequence shown in SEQ ID NO: 4 can be mentioned. The length of the partial sequence is not particularly limited as long as it induces CTL that recognizes T cell epitope consisting of the amino acid sequence shown in SEQ ID NO: 3. For example, it is not more than 500 amino acids, not more than 400 amino acids, not more than 300 amino acids, not more than 200 amino acids, not more than 100 amino acids, not more than 90 amino acids, not more than 80 amino acids, not more than 70 amino acids, not more than 60 amino acids, not more than 50 amino acids, not more than 40 amino acids, not more than 30 amino acids, not more than 20 amino acids, not more than 15 amino acids, or not more than 10 amino acids. A polypeptide consisting of the amino acid sequence shown in SEQ ID NO: 3 can also be used as an M1 fragment containing conserved T cell epitope in the present invention.

As the NP fragment containing conserved T cell epitope, a polypeptide containing the amino acid sequence shown in SEQ ID NO: 5, and a partial sequence of the amino acid sequence shown in SEQ ID NO: 6 can be mentioned. The length of the partial sequence is not particularly limited as long as it induces CTL that recognizes T cell epitope consisting of the amino acid sequence shown in SEQ ID NO: 5. For example, it is not more than 500 amino acids, not more than 400 amino acids, not more than 300 amino acids, not more than 200 amino acids, not more than 100 amino acids, not more than 90 amino acids, not more than 80 amino acids, not more than 70 amino acids, not more than 60 amino acids, not more than 50 amino acids, not more than 40 amino acids, not more than 30 amino acids, not more than 20 amino acids, not more than 15 amino acids, or not more than 10 amino acids. A polypeptide consisting of the amino acid sequence shown in SEQ ID NO: 5 can also be used as an NP fragment containing conserved T cell epitope in the present invention.

Dengue virus contains, in N3, a T cell epitope conserved among subtypes. Thus, N3 or N3 fragment containing the conserved T cell epitope can be used as a virus antigen or a fragment thereof containing T cell epitope conserved among subtypes.

The size of the conserved T cell epitope-containing antigen or a fragment thereof is not particularly limited and it is generally not more than 2000 amino acids (e.g., not more than 1000 amino acids, not more than 750 amino acids, not more than 600 amino acids, not more than 500 amino acids, not more than 400 amino acids, or not more than 300 amino acids).

The fusion polypeptide of the present invention has an oligomerization activity. In the present invention, the oligomerization activity means an activity causing non-covalent association of the same molecules to form an oligomer. That is, the fusion polypeptide of the present invention means an activity for association of the same molecules to form an oligomer. The size of the oligomer (number of monomers constituting one oligomer) is generally 2-50 mer, preferably 8-25 mer, but it is not particularly limited.

Since M1 generally forms 2-20 mer, when M1 is used as the conserved T cell epitope-containing antigen, the size of the oligomer may be generally 2-20 mer, preferably 8-20 mer. Since HA naturally forms 3 mer, when HA is used as the conserved B cell epitope-containing antigen, the size of the oligomer may be generally a multiple of 3, for example, 3-21 mer, preferably 9-21 mer.

In one embodiment, when the above-mentioned (a) conserved B cell epitope-containing antigen or a fragment thereof and/or (b) conserved T cell epitope-containing antigen or a fragment thereof have/has an oligomerization activity, the fusion polypeptide itself of the present invention has an oligomerization activity. For example, M1 of influenza A virus has an oligomerization activity. When M1 or a fragment thereof is used as (b) conserved T cell epitope-containing antigen or a fragment thereof as mentioned above, since it has an oligomerization activity, the fusion polypeptide of the present invention itself also has an oligomerization activity. The oligomerization activity region of M1 of influenza A virus is known to be mainly present in 87-165 region of SEQ ID NO: 4 (oligomerization region) (SEQ ID NO: 7) (non-patent document 15). When a fragment of M1 is used as a fragment of conserved T cell epitope-containing antigen, the fragment preferably contains the oligomerization region (SEQ ID NO: 7) in addition to the conserved T cell epitope (SEQ ID NO: 3). Being oligomerized, the fusion polypeptide of the present invention is expected to have high immunogenicity compared to monomer.

In one embodiment, the fusion polypeptide of the present invention contains (c) polypeptide having an oligomerization activity in addition to (a) conserved B cell epitope-containing antigen or a fragment thereof and (b) conserved T cell epitope-containing antigen or a fragment thereof, due to which the fusion polypeptide itself of the present invention has an oligomerization activity. This embodiment is useful as a method for conferring an oligomerization activity to the fusion polypeptide of the present invention when (a) conserved B cell epitope-containing antigen or a fragment thereof and/or (b) conserved T cell epitope-containing antigen or a fragment thereof do/does not have an oligomerization activity. Examples of the polypeptide having an oligomerization activity include, but are not limited to, M1 of influenza A virus or a fragment thereof having an oligomerization activity, ferritin, heat shock protein, complement protein family, lectin protein family, actin and the like.

While the size of the polypeptide having an oligomerization activity is not particularly limited, it is generally not more than 2000 amino acids (e.g., not more than 1000 amino acids, not more than 750 amino acids, not more than 600 amino acids, not more than 500 amino acids, not more than 400 amino acids, or not more than 300 amino acids).

In the fusion polypeptide of the present invention, either (a) conserved B cell epitope-containing antigen or a fragment of the antigen, or (b) conserved T cell epitope-containing antigen or a fragment of the antigen may be located on the N-terminus side. That is, the sites (a) and (b) may be located in any order of (a)→(b) and (b)→(a) from the N-terminus to the C-terminus.

When the fusion polypeptide of the present invention contains (c) polypeptide having an oligomerization activity, the order of arrangement of (a) conserved B cell epitope-containing antigen or a fragment thereof, (b) conserved T cell epitope-containing antigen or a fragment thereof, and (c) polypeptide having an oligomerization activity is not particularly limited. That is, the sites (a), (b), and (c) may be located in any order of (a)→(b)→(c), (a)→(c)→(b), (b)→(a)→(c), (b)→(c)→(a), (c)→(a)→(b), and (c)→(b)→(a) from the N-terminus to the C-terminus.

The sites (a) and (b) (and optionally (c)) may be directly linked to each other by a bond or may be linked via a linker polypeptide. From the aspect of avoiding inaccessibility to epitope due to steric hindrance, the sites (a) and (b) (and optionally (c)) are preferably linked to each other via a linker polypeptide. The length of the linker polypeptide is not particularly limited as long as the fusion polypeptide of the present invention induces a humoral immune response and a cellular immune response to the target virus. When it is too long, the risk of causing an unnecessary immune induction due to the linker polypeptide increases. Therefore, the length of the linker polypeptide is preferably set to generally 1-100 amino acids, preferably 1-50 amino acids, more preferably 1-25 amino acids, or further preferably 1-amino acids. Examples of the linker polypeptide include, but are not limited to, linker peptides constituted of multiple tandem-linked flexible peptides without a secondary structure which are composed of glycine, serine and the like by peptide bond, for example, (GlyGlyGlyGlySer)n.

The fusion polypeptide of the present invention optionally has an additional sequence on the N-terminus from (a) or (b) (or optionally (c)) which is located most closely to the N-terminus, and/or the C-terminus from (a) or (b) (or optionally (c)) which is located most closely to the C-terminus. The length of the additional sequence is not particularly limited as long as the fusion polypeptide of the present invention induces a humoral immune response and a cellular immune response to the target virus. When it is too long, the risk of causing an unnecessary immune induction due to the additional sequence increases. Therefore, the length of the additional sequence is preferably set to generally 1-100 amino acids, preferably 1-50 amino acids, more preferably 1-amino acids, or further preferably 1-15 amino acids.

In one embodiment, the additional sequence may be a tag sequence for facilitating purification and detection of the fusion polypeptide of the present invention. While the kind of the tag sequence is not particularly limited, for example, FLAG (Hopp, T. P. et al., BioTechnology (1988) 6, 1204-1210), 6×His-10×His consisting of 6-10 His (histidine) residues, fragment of human c-myc, fragment of α-tubulin, B-tag, fragment of Protein C, GST (glutathione-S-transferase), β-galactosidase, MBP (maltose binding protein) and the like can be mentioned.

In one embodiment, the fusion polypeptide of the present invention does not have an additional sequence on the N-terminus from (a) or (b) (or optionally (c)) which is located most closely to the N-terminus, and/or the C-terminus from (a) or (b) (or optionally (c)) which is located most closely to the C-terminus.

The length of the fusion polypeptide of the present invention is not particularly limited as long as it induces a humoral immune response and a cellular immune response to the target virus. It is generally not more than 10000 amino acids (e.g., not more than 8000 amino acids, not more than 6000 amino acids, not more than 4000 amino acids, not more than 2000 amino acids, or not more than 1000 amino acids).

The fusion polypeptide of the present invention can be produced using a well-known recombinant protein production method.

The present invention also provides an oligomer of the above-mentioned fusion polypeptide of the present invention. Since the fusion polypeptide of the present invention has an oligomerization activity, the fusion polypeptides of the present invention non-covalently associate in an aqueous solution to form an oligomer. The size of the oligomer of the present invention (number of monomers (the fusion polypeptides of the present invention) constituting one oligomer) is generally 2-50 mer, preferably 8-20 mer, but it is not particularly limited. Since M1 generally forms 2-20 mer, when M1 is used as the conserved T cell epitope-containing antigen, the size of the oligomer may be generally 2-20 mer, preferably 8-20 mer. Since HA naturally forms 3 mer, when HA is used as the conserved B cell epitope-containing antigen, the size of the oligomer may be generally a multiple of 3, for example, 3-21 mer, preferably 9-21 mer. The oligomer of the present invention is expected to have high immunogenicity compared to monomer of the fusion polypeptide of the present invention.

In one preferable embodiment, the present invention provides a fusion polypeptide that induces a humoral immune response and a cellular immune response to influenza A virus, comprising antigens or fragments thereof of the following (a1) and (b1) and having an oligomerization activity:

(a1) influenza A virus HA or a fragment thereof each containing stem region consisting of Gln 310-Asp 390 of the amino acid sequence shown in SEQ ID NO: 1; and (b1) influenza A virus M1 or a fragment thereof containing T cell epitope consisting of the amino acid sequence shown in SEQ ID NO: 3, (wherein (b1) influenza A virus M1 or a fragment thereof has oligomerization activity).

The fusion polypeptide can induce humoral immune response and cellular immune response to influenza A virus having HA containing the three-dimensional structural epitope in a stem region consisting of Gln 310-Asp 390 of the amino acid sequence shown in SEQ ID NO: 1, and M1 containing T cell epitope consisting of the amino acid sequence shown in SEQ ID NO: 3. The influenza A virus may be type A1 or type A3. The fusion polypeptide induces anti-influenza A virus HA antibody that recognizes and binds to three-dimensional structural epitope in a stem region consisting of Gln 310-Asp 390 of the amino acid sequence shown in SEQ ID NO: 1, and CTLs that recognizes T cell epitope consisting of the amino acid sequence shown in SEQ ID NO: 3.

In (a1), when HA fragment of influenza A virus when an HA fragment of influenza A virus is used which contains the three-dimensional structural epitope in stem region consisting of Gln 310-Asp 390 of the amino acid sequence shown in SEQ ID NO: 1, the length of the fragment is not particularly limited as long as it induces an antibody that recognizes and binds to the three-dimensional structural epitope in the stem region consisting of Gln 310-Asp 390 of the amino acid sequence shown in SEQ ID NO: 1. For example, it is not more than 500 amino acids, not more than 400 amino acids, not more than 300 amino acids, not more than 200 amino acids, not more than 100 amino acids, not more than 90 amino acids, not more than 80 amino acids, not more than 70 amino acids, not more than 60 amino acids, not more than 50 amino acids, not more than 40 amino acids, not more than 30 amino acids, not more than 20 amino acids, not more than 15 amino acids, or not more than 10 amino acids. As the HA fragment, a polypeptide consisting of a partial sequence of the amino acid sequence shown in SEQ ID NO: 1 and containing a stem region consisting of Gln 310-Asp 390 of the amino acid sequence shown in SEQ ID NO: 1 can be mentioned. The length of the partial sequence is not particularly limited as long as it induces an antibody that recognizes and binds to the three-dimensional structural epitope in the stem region consisting of Gln 310-Asp 390 of the amino acid sequence shown in SEQ ID NO: 1. For example, it is not more than 500 amino acids, not more than 400 amino acids, not more than 300 amino acids, not more than 200 amino acids, not more than 100 amino acids, not more than 90 amino acids, not more than 80 amino acids, not more than 70 amino acids, not more than 60 amino acids, not more than 50 amino acids, not more than 40 amino acids, not more than 30 amino acids, not more than 20 amino acids, not more than 15 amino acids, or not more than 10 amino acids. A polypeptide consisting of Gln 310-Asp 390 of the amino acid sequence shown in SEQ ID NO: 1 can also be used as an HA fragment in the present invention. Preferable examples of the HA fragment include a head-lacking HA in which signal peptide and head region are deleted from full-length HA, and a fragment thereof containing the three-dimensional structural epitope in a stem region consisting of Gln 310-Asp 390 of the amino acid sequence shown in SEQ ID NO: 1. An example of the amino acid sequence of the head-lacking HA is shown in SEQ ID NO: 2.

In (b1), when M1 fragment of influenza A virus which the fragment containing T cell epitope consisting of the amino acid sequence shown in SEQ ID NO: 3 is used, the length of the fragment is not particularly limited as long as it induces CTL that recognizes and binds to a T cell epitope consisting of the amino acid sequence shown in SEQ ID NO: 3. For example, it is not more than 500 amino acids, not more than 400 amino acids, not more than 300 amino acids, not more than 200 amino acids, not more than 100 amino acids, not more than 90 amino acids, not more than 80 amino acids, not more than 70 amino acids, not more than 60 amino acids, not more than 50 amino acids, not more than 40 amino acids, not more than 30 amino acids, not more than 20 amino acids, not more than 15 amino acids, or not more than 10 amino acids. As the fragment, a polypeptide consisting of a partial sequence of the amino acid sequence shown in SEQ ID NO: 4 and containing the amino acid sequence shown in SEQ ID NO: 3 can be mentioned. The length of the partial sequence is not particularly limited as long as it induces CTL that recognizes T cell epitope consisting of the amino acid sequence shown in SEQ ID NO: 3. For example, it is not more than 500 amino acids, not more than 400 amino acids, not more than 300 amino acids, not more than 200 amino acids, not more than 100 amino acids, not more than 90 amino acids, not more than 80 amino acids, not more than 70 amino acids, not more than 60 amino acids, not more than 50 amino acids, not more than 40 amino acids, not more than 30 amino acids, not more than 20 amino acids, not more than 15 amino acids, or not more than 10 amino acids. A polypeptide consisting of the amino acid sequence shown in SEQ ID NO: 3 can also be used as a fragment of M1 containing conserved T cell epitope in the present invention.

influenza A virus M1 or a fragment thereof of (b1) has an oligomerization activity since it contains an oligomerization region of M1 (SEQ ID NO: 7).

In the fusion polypeptide of this embodiment, the site of either (a1) or (b1) may be located on the N-terminus. That is, the sites (a1) and (b1) may be located in any order of (a1)→(b1) and (b1)→(a1) from the N-terminus to the C-terminus.

The sites (a1) and (b1) may be linked directly by a bond or may be linked via a linker polypeptide. From the aspect of avoiding inaccessibility to epitope due to steric hindrance, the sites (a1) and (b1) are preferably linked to each other via a linker polypeptide. The length of the linker polypeptide is preferably set to generally 1-100 amino acids, preferably 1-50 amino acids, more preferably 1-25 amino acids, or further preferably 1-15 amino acids.

The fusion polypeptide of this embodiment optionally has an additional sequence on the N-terminus from (a1) or (b1) which is located most closely to the N-terminus, and/or the C-terminus from (a1) or (b1) which is located most closely to the C-terminus. The length of the additional sequence is preferably set to generally 1-100 amino acids, preferably 1-50 amino acids, more preferably 1-25 amino acids, further preferably 1-15 amino acids. The additional sequence may be a tag sequence for facilitating purification and detection of the fusion polypeptide of the present invention.

In one embodiment, the fusion polypeptide of this embodiment does not have an additional sequence on the N-terminus from (a1) or (b1) which is located most closely to the N-terminus, and/or the C-terminus from (a1) or (b1) which is located most closely to the C-terminus.

The length of the fusion polypeptide of this embodiment is not particularly limited as long as it induces a humoral immune response and a cellular immune response to influenza A virus. It is generally not more than 10000 amino acids (e.g., not more than 8000 amino acids, not more than 6000 amino acids, not more than 4000 amino acids, not more than 2000 amino acids, or not more than 1000 amino acids).

A specific example of the fusion polypeptide of this embodiment is shown in FIG. 3. The upper panel (SEQ ID NO: 8) of FIG. 3 shows one example of the amino acid sequence of a fusion polypeptide of the mature type influenza virus HA and M1. The lower panel (SEQ ID NO: 9) of FIG. 3 shows one example of the amino acid sequence of a fusion polypeptide of the mature type head-lacking influenza virus HA and M1.

Nucleocapsid protein (NP) of influenza A virus associates with M1 at neutral pH. Therefore, a complex of the fusion polypeptide of this embodiment and NP is formed by mixing the fusion polypeptide of this embodiment and influenza A virus NP at neutral pH. Since NP and M1 associate at a ratio of 1:1, the mixing molar ratio (fusion polypeptide:NP) is usually 1:0.5-2, or preferably 1:1. The present invention also provides such complex. The complex of the present invention contains NP in addition to (a1) influenza A virus HA or a fragment thereof each containing the three-dimensional structural epitope in a stem region consisting of Gln 310-Asp 390 of the amino acid sequence shown in SEQ ID NO: 1; and (b1) influenza A virus M1 or a fragment thereof containing T cell epitope consisting of the amino acid sequence shown in SEQ ID NO: 3. As mentioned above, since NP contains T cell epitope conserved among subtypes of influenza A virus, the complex of the present invention is expected to more strongly induce humoral immune response and cellular immune response to influenza A virus. The influenza A virus may be type A1 (e.g., H1N1) or type A3 (e.g., H3N2). The complex of the present invention induces anti-influenza A virus HA antibody that recognizes and binds to the three-dimensional structural epitope in a stem region consisting of Gln 310-Asp 390 of the amino acid sequence shown in SEQ ID NO: 1, CTL that recognizes T cell epitope consisting of the amino acid sequence shown in SEQ ID NO: 3, and CTL that recognizes T cell epitope in NP.

The present invention also provides an oligomer of the above-mentioned fusion polypeptide or a complex of this embodiment (FIG. 1). Since the fusion polypeptide of this embodiment has an oligomerization activity since it contains M1 or a fragment thereof, the fusion polypeptides of this embodiment non-covalently associate in an aqueous solution to form an oligomer. Since HA also naturally forms a trimer, the fusion polypeptide of this embodiment is expected to easily undergo oligomerization due to a synergistic effect with the oligomerization activity of M1. When the above-mentioned complex is oligomerized, first, the fusion polypeptide of this embodiment is oligomerized to obtain an oligomer of the fusion polypeptide. Then, the oligomer of the fusion polypeptide of this embodiment is mixed with NP at a neutral pH (e.g., pH 6.5-7.5) and NP is associated with M1 or a fragment thereof in the fusion polypeptide to form a complex. As a result, an oligomer of the above-mentioned complex is obtained (FIG. 1). The mixing molar ratio (fusion polypeptide:NP) is generally 1:0.5-2, preferably 1:1. The size of the oligomer of this embodiment (the number of monomers constituting one oligomer (fusion polypeptide or complex of this embodiment)) is not particularly limited and is generally 3-21 mer, or preferably 9-21 mer. The oligomer of this embodiment is expected to have a higher immunogenicity compared to the monomer of the fusion polypeptide or complex of this embodiment.

2. Pharmaceutical Composition

The present invention provides a pharmaceutical composition containing the above-mentioned fusion polypeptide, complex, or oligomer of the present invention. The pharmaceutical composition of the present invention can be obtained by formulating the above-mentioned fusion polypeptide, complex, or oligomer thereof of the present invention according to a conventional means. The pharmaceutical composition of the present invention contains the fusion polypeptide, complex, or oligomer thereof of the present invention and a pharmaceutically acceptable carrier.

Examples of the pharmaceutically acceptable carrier include, but are not limited to, excipients such as sucrose, starch, mannitol, sorbitol, lactose, glucose, cellulose, talc, calcium phosphate, calcium carbonate and the like, binders such as cellulose, methylcellulose, hydroxypropylcellulose, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerogel, talc, sodium lauryl sulfate and the like, aromatics such as citric acid, menthol, glycyrrhizin.ammonium salt, glycine, orange powder and the like, preservatives such as sodium benzoate, sodium bisulfite, methylparaben, propylparaben and the like, stabilizers such as citric acid, sodium citrate, acetic acid and the like, suspending agents such as methylcellulose, polyvinylpyrrolidone, aluminum stearate and the like, dispersing agents such as surfactant and the like, diluents such as water, saline and the like, base waxes such as cacao butter, polyethylene glycol, kerosene and the like, and the like.

The pharmaceutical composition of the present invention may further contain an adjuvant to potentiate the immune response induction effect of the fusion polypeptide, a complex, or an oligomer thereof of the present invention. Examples of the adjuvant include, but are not limited to, aluminum hydroxide, complete Freund's adjuvant, incomplete Freund's adjuvant, pertussis adjuvant, poly(I:C), CpG-DNA and the like.

Such pharmaceutical composition is provided in a dosage form suitable for oral or parenteral administration (preferably parenteral administration).

As a composition for parenteral administration, for example, injection, suppository and the like are used. Injection may include dosage forms such as intravenous injection, subcutaneous injection, intradermal injection, muscular injection, drip injection and the like. Such injections can be prepared according to a known method. As a production method of injection, the above-mentioned oligodeoxynucleotide or complex of the present invention is dissolved or suspended in an aseptic aqueous solvent generally used for injection. As the aqueous solvent for injection, distilled water; physiological brine; buffers such as phosphate buffer, carbonate buffer, tris buffer, acetate buffer and the like, and the like can be used. The pH of such aqueous solvent is, for example, 5-10, or preferably 6-8. The prepared injection is preferably filled in a suitable ampoule.

Moreover, powder preparations of the fusion polypeptide, complex, or oligomer thereof of the present invention can also be obtained by subjecting a solution or suspension of the fusion polypeptide, complex, or oligomer thereof of the present invention to a treatment such as vacuum drying, freeze drying and the like. The fusion polypeptide, complex, or oligomer thereof of the present invention can be stored in a powder state and used by dispersing the powder with an aqueous solvent for injection when in use.

The content of the fusion polypeptide, complex, or oligomer thereof of the present invention in a pharmaceutical composition is generally about 0.1-100 wt %, preferably about 1-99 wt %, or further preferably about 10-90 wt %, of the whole pharmaceutical composition.

3. Pharmaceutical Use

The fusion polypeptide, complex, or oligomer thereof of the present invention induces immune responses (humoral immune response and cellular immune response) to a virus and prevents or treats the viral infectious disease. Administration of the fusion polypeptide, complex, oligomer thereof, or pharmaceutical composition of the present invention to mammals (primates such as human and the like, rodents such as mouse and the like) induces immune responses (humoral immune response and cellular immune response) to the virus in the mammals and the viral infectious disease can be prevented or treated. The fusion polypeptide of the present invention contains an antigen or fragment thereof containing a B cell epitope conserved among subtypes of the virus, and an antigen or a fragment thereof containing a T cell epitope conserved among subtypes of the virus. Thus, it induces humoral immune response (antibody (preferably neutralizing antibody) production) and cellular immune response (CTL proliferation) with effective cross-reactivity with variant viruses and a wide range of subtypes, and can prevent or treat infectious diseases of the virus as an effective vaccine that cross-reacts with various subtypes of viruses.

For example, the fusion polypeptide, the complex, the oligomer thereof, or the pharmaceutical composition of the present invention is administered to a patient with the viral infection disease or mammals (primates such as human and the like, rodents such as mouse and the like) that may be infected with the virus to induce humoral immune response and cellular immunity to the virus in the subject that received the administration, that is, defense immune response of the mammal is induced, whereby the viral infectious diseases can be prevented or treated. The fusion polypeptide, the complex, the oligomer thereof, or the pharmaceutical composition of the present invention is administered to mammals (primates such as human and the like, rodents such as mouse and the like) that may be infected with the virus to induce humoral immune response and cellular immunity to the virus in the subject that received the administration, that is, a defense immune response of the mammal is induced, whereby the risk of infection with the virus can be reduced.

For example, a fusion polypeptide that induces humoral immune response and cellular immune response to influenza A virus, comprising antigens or fragments thereof of the following (a1) and (b1) and having an oligomerization activity:

(a1) influenza A virus HA or a fragment thereof each containing the three-dimensional structural epitope in a stem region consisting of Gln 310-Asp 390 of the amino acid sequence shown in SEQ ID NO: 1; and (b1) influenza A virus M1 or a fragment thereof containing T cell epitope consisting of the amino acid sequence shown in SEQ ID NO: 3, (wherein (b1) influenza A virus M1 or a fragment thereof has oligomerization activity);

a complex of the fusion polypeptide and influenza A virus NP: an oligomer of the fusion polypeptide or a complex; or a pharmaceutical composition containing the fusion polypeptide, the complex, or the oligomer is administered to a patient with a influenza A virus infectious disease or mammals (primates such as human and the like, rodents such as mouse and the like) that may be infected with influenza A virus to induce immune responses (humoral immune response and cellular immune response) to the influenza A virus in the mammal, whereby influenza A virus infectious diseases can be prevented or treated. More particularly, humoral immune response and cellular immune response (production of anti-influenza A virus HA antibody that recognizes and binds to the three-dimensional structural epitope in a stem region consisting of Gln 310-Asp 390 of the amino acid sequence shown in SEQ ID NO: 1 and proliferation of CTL that recognizes T cell epitope consisting of the amino acid sequence shown in SEQ ID NO: 3) to influenza A virus (e.g., type A1 influenza virus (e.g., H1N1) and type A3 (e.g., H3N2)) having HA containing B cell epitope consisting of the amino acid sequence shown in SEQ ID NO: 1, and M1 containing T cell epitope consisting of the amino acid sequence shown in SEQ ID NO: 3 are induced, whereby influenza A virus infectious diseases can be prevented or treated. A pharmaceutical composition containing the fusion polypeptide, the complex, or the oligomer is administered to mammals (primates such as human and the like, rodents such as mouse and the like) that may be infected with influenza A virus to induce immune responses (humoral immune response and cellular immune response) to the influenza A virus in the mammal, whereby the risk of influenza A virus infection can be reduced. A pharmaceutical composition containing the fusion polypeptide, the complex, or the oligomer is useful as a vaccine that cross-reacts with a wide range of subtypes of influenza A viruses, including seasonal influenza viruses and the expected highly pathogenic pandemic influenza viruses, and is expected to be effective.

The present invention is explained in more detail in the following Examples. The present invention is not limited in any manner by these Examples.

[Synthesis of Gene]

From the sequence of the influenza virus, Michigan strain, a gene was designed (SEQ ID NO: 10) in which a nucleotide encoding a head-lacking type hemagglutinin and a nucleotide encoding a matrix protein were linked with a nucleotide encoding a GS linker (SEQ ID NO: 12) interposed between them, and a nucleotide encoding 6×His tag (SEQ ID NO: 13) was further added to the C-terminus. From this sequence, a sequence was artificially synthesized in which an EcoRV sequence and an initiation codon (ATG) were added to the 5'-terminus, and a stop codon (TGA) and a NotI sequence were added to the 3'-terminus. Using the added restriction enzyme sites, the synthesized sequence was inserted between EcoRV and NotI in MCS of pEU-EU1-MCS (Cell-Free Sciences Co., Ltd.), which is a protein expression vector exclusively for wheat cell-free system. The inserted sequence was confirmed to have no mutation by sequence analysis. The obtained plasmid was prepared in large amounts by using *Escherichia coli* DHS.

[Synthesis of Antigen Protein]

Using the plasmid as a template and utilizing SP6 promoter on the plasmid, a transcription reaction was carried out at 37° C. for 6 hr to synthesize mRNA. Using the synthesized mRNA, a translation reaction was carried out at 15° C. for 20 hr by a multilayer method (reaction scale 6 mL scale×12 reactions). As the wheat germ extract, WEPRO7240H optimized for the synthesis/purification of His-tag fusion protein was used. The synthesized protein (crude) solution was centrifuged (21,600×g, 4° C., 10 min), and the precipitate fraction was washed twice with a translation buffer. This precipitate fraction was solubilized with a solubilizer to obtain an antigen protein (head-lacking HA-M1 fusion protein (+GS linker+6×His tag), SEQ ID NO: 11) (FIG. 4).

[Analysis of Antigen Specific Reaction Behavior of T Cell to Influenza Virus Antigen (HA-M1 Antigen)]

Test Method

Five BALB/cAJcl mice (♀) were prepared, and subcutaneously immunized with 25 μl each of HA-M1/Complete Freund Ajuvant (250 μg/ml) on the foot-pad and 50 μl on the base of tail. On day 7, the mice were dissected and inguinal and popliteal lymph nodes were collected. The collected lymph nodes were ground with a mesh to prepare a cell dispersion. Antigen dilution solution for coculture was prepared and the concentration in the well was set to 100, 50, 25, or 0 μg/ml. A single cell dispersion ($5\times10^5$ cells/well) was stimulated with HA-M1 antigen solution (0, 25, 50, or 100 μg/ml) for 92 hr, and then the proliferation level of lymph node cells was evaluated. In addition, the concentrations of IL-10 and IFN-γ in the culture supernatant were measured by ELISA method. That is, after collecting the supernatant, the medium was replenished, and CCK-8 (Cell Counting Kit-8: DOJINDO LABORATORIES) diluted 2 times with the medium was added to each well at 20 μl/well, and the number of cells in each well was calculated by measuring the absorbance (450 nm) after 3 hr from the addition. On the other hand, the culture supernatant was diluted 2 times (IL-10) and 20 times (IFN-γ), and measurement was performed using Mouse IL-10 Duoset ELISA (R&D) and Mouse IFN-γ Duoset ELISA (R&D) kit.

Results

Figure 5:
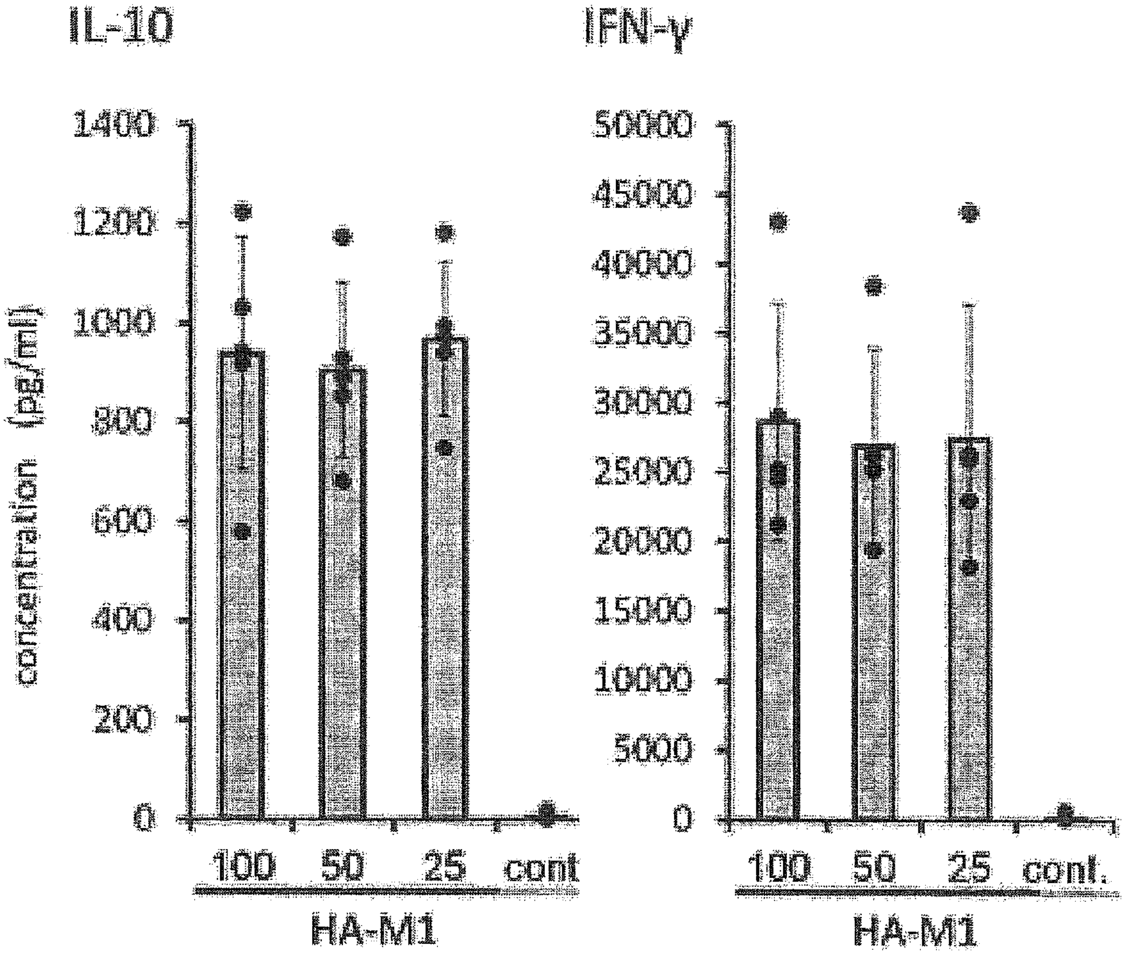
FIG. 5 shows the result of quantification of cytokine (IL-10 and IFN-γ) in supernatant obtained by collecting cells from a lymph node of a mouse inoculated with HA-M1 antigen, adding HA-M1 antigen (0 (control), 25, 50, or 100 μg/ml), and culturing the cells for 92 hr.
Figure 6:
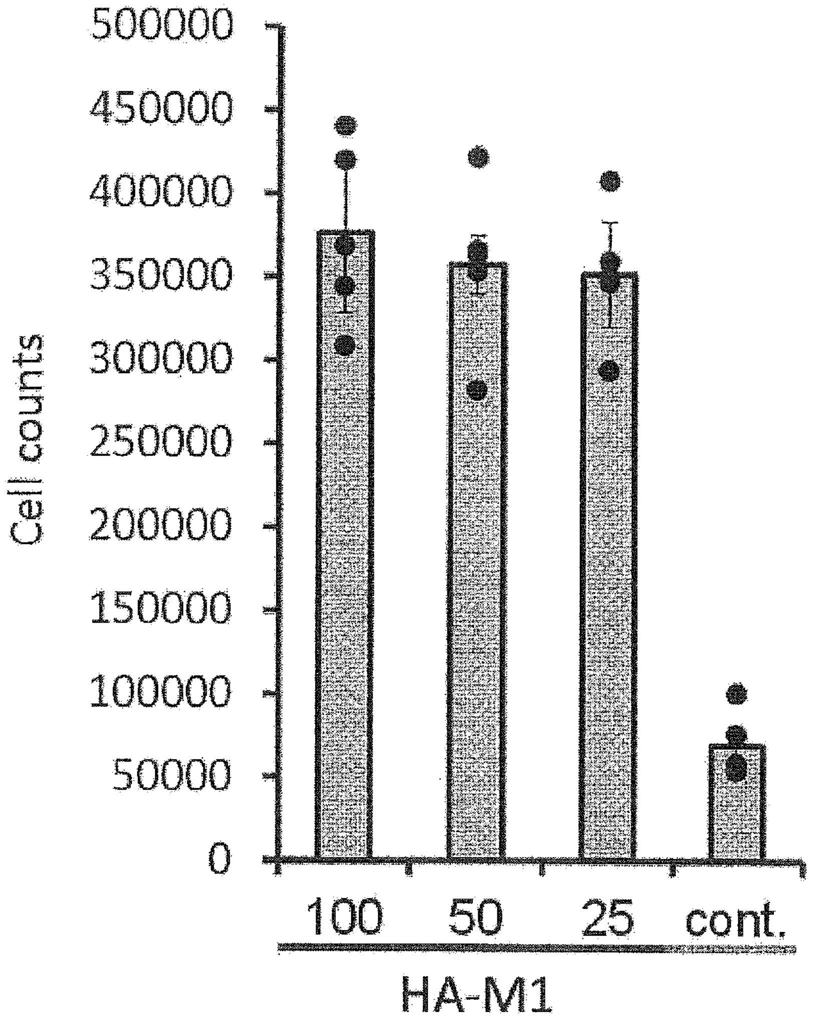
FIG. 6 shows the result of count of cells obtained by collecting cells from a lymph node of a mouse inoculated with HA-M1 antigen, adding HA-M1 antigen (0 (control), 25, 50, or 100 μg/ml), and culturing the cells for 92 hr.

The results regarding activation of HA-M1 antigen-specific T cells are shown in FIG. 5. Since the T cell subset, Th1, produces IFN-γ, and Th2 produces IL-10, the concentration of these cytokines was measured. Since the production of these cytokines was dramatically promoted, this HA-M1 antigen is considered a superior candidate as a vaccine antigen capable of inducing humoral immunity and cellular immunity. In addition, the results regarding HA-M1 antigen-specific lymph node cell proliferation are shown in FIG. 6. When HA-M1 antigen was added to the lymph node cells of mice immunized with HA-M1 antigen and the cells were cultured, remarkable cell proliferation was observed at antigen concentrations of 25, 50, and 100 μg/ml. The antigen concentration is considered to be saturated because there is no significant difference in cell proliferation activation depending on the antigen concentration. It was shown that the antigen-presenting cells present in the cultured cells take in and digest HA-M1 antigen to produce peptide antigen and the peptide antigen is presented by histocompatibility complex (MHC class I), thus resulting in activation of T cells.

[Influenza Virus Neutralization Activity of Serum of HA-M1 Antigen-Administered Mouse]

Method

Three BALB/cAJcl mice (♀) were prepared for each test group, and immunized by intraperitoneal administration of HA-M1 antigen solution at 50 or 100 μg/head+Alum 2 mg/head (Imject alum, Thermo: #77161, Lot TE267860B). Immunization was carried out twice on day 0 and day 11. The test groups consisted of a group in which blood was collected on day 14 from the first immunization day (#1-#3), a group in which blood was collected on day 21 (#4-#6), and a control group ((#7-#9)). Serum was collected by collecting the whole blood under anesthesia. The obtained serum was inactivated by incubating at 56° C. for 45 min.

Two-fold serial dilution from 10-fold diluted solution of each serum was performed, 50 μl of serum diluted solution, 200TCID$_{50}$ influenza virus type A1 (A/Michigan/45/2015 (H1N1pdm09)) and 50 μl of influenza virus type A3 (A/Hong Kong/4801/2014(H3N2)) were mixed and reacted at 37° C. for 30 min, MDCK cells cultured in a 48 well plate were infected therewith, trypsin-added medium (100 μl) was added, the cells were cultured for 4 days, and the neutralizing antibody titer was measured in the presence or absence of cytopathy.

Results

There was no difference in the neutralizing activity against influenza A virus subtypes H1N1 and H3N2 between the control group and the antigen administration group whose blood was collected on day 14; however, the neutralization activity was superior in the antigen administration group whose blood was collected on day 21 (Table 1). Neutralizing activity that cross-reacts with H3N2 type was obtained by immunization with a fusion protein antigen of type A H1N1 head-lacking HA and M1. Thus, it was confirmed the antigens constructed in the present invention have a neutralization epitope common to influenza A virus subtypes.

TABLE 1 serum neutralizing antibody titer against influenza virus in HA-M1 antigen-administered mouse

| BALB/c mouse (♀) | HA-M1 dose (μg) | immunity period (days) | A/Michigan/ 45/2015 (H1N1pdm09) | A/Hong Kong/ 4801/2014 (H3N2) |
|---|---|---|---|---|
| #1 | 50 | 14 | <20 | <20 |
| #2 | 50 | 14 | <20 | <20 |
| #3 | 50 | 14 | <20 | <20 |
| #4 | 100 | 21 | 40 | 40 |
| #5 | 100 | 21 | 40 | 40 |
| #6 | 100 | 21 | 40 | 20 |
| #7 | 0 | 21 | <20 | <20 |
| #8 | 0 | 21 | <20 | <20 |
| #9 | 0 | 21 | <20 | <20 |

[Efficacy Test in Influenza Virus-Infected Mouse]

Using mice (BALE/c, female, 5-week-old), the following 4 groups were tested.

test group 1: antigen protein administration×H1N1 type influenza virus inoculation (6 mice)

test group 2: phosphate buffered saline administration× H1N1 type influenza virus inoculation (5 mice)

test group 3: antigen protein administration×H3N2 type influenza virus inoculation (6 mice)

test group 4: phosphate buffered saline administration× H3N2 type influenza virus inoculation (5 mice)

Mice were bred at 3-5 heads/cage in an environment of room temperature 24±3° C., humidity 50±20%, ventilation 10-25 times/hr, and lighting 12 hr. The feed was fed by free intake of MF (Oriental Yeast Co., Ltd.). As an antigen protein administration method, an antigen protein (protein concentration 250 μg/mL) added with an equal amount of Imject Alum Adjuvant (Thermo Fisher Scientific K.K.) was prepared, and 0.2 mL per mouse was administered 2 times with 7-day interval (total 0.4 mL) by subcutaneous injection. In test groups 2 and 4, the same adjuvant as in test groups 1 and 3 was added to phosphate buffered saline and administered in the same manner. Influenza virus inoculation was carried out by transnasal inoculation of 50 μL of the inoculation virus under isoflurane anesthesia on day 7 after the second antigen protein administration. The influenza viruses used were 2 subtypes of H1N1 (strain name: A/PR/8/34, ATCC No.: VR-1469, BSL: 2, virus titer: $1.6\times10^8$TCID$_{50}$/mL) and H3N2 (strain name: A/Port Chalmers/1/73, ATCC No.: VR-810, BSL: 2, virus titer: $1.3\times10^7$TCID$_{50}$/mL). To understand the condition of the mice, the body weight was measured on the arrival date of the mouse, 14 days before the virus inoculation (Day −14), 7 days before (Day −7), the day of virus inoculation (Day 0), 3 days after (Day 3), 7 days after (Day 7), 10 days after (Day 10), and 14 days after (Day 14) the day of virus inoculation. In addition, the general condition of the mice (decreased activity and coarse fur) was also evaluated during the period from 14 days before the virus inoculation day to 14 days after the virus inoculation day.

Figure 7:
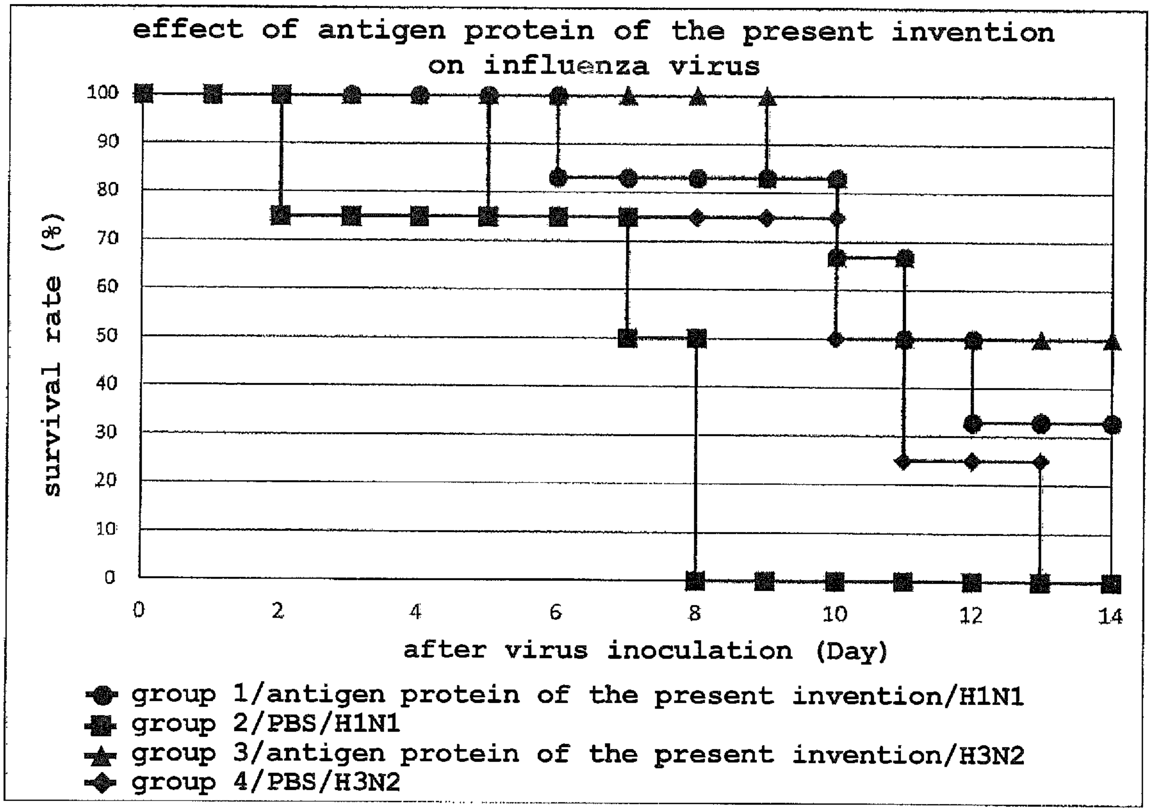
FIG. 7 shows that mice immunized with the antigen protein of the present invention acquired resistance to influenza virus and showed increased survival rates.

The results are shown in the following Table 2-1 and Table 2-2 (general condition), Table 3 (body weight), and Table 4 (survival rate). A graph relating to survival rate is shown in FIG. 7.

TABLE 2-1

General condition

| group | number of mice | general condition | score | Day (virus inoculation day as Day0) −14 | −13 | −12 | −11 | −10 | −9 | −8 | −7 | −6 | −5 | −4 | −3 | −2 | −1 | 0 |
|---|---|---|---|---|---|---|---|---|---|---|---|---|---|---|---|---|---|---|
| group 1 | 6 | decrease | 0 | 6 | 6 | 6 | 6 | 6 | 6 | 6 | 6 | 6 | 6 | 6 | 6 | 6 | 6 | 6 |
| H1N1 | | in | 1 | 0 | 0 | 0 | 0 | 0 | 0 | 0 | 0 | 0 | 0 | 0 | 0 | 0 | 0 | 0 |
| virus/ | | activity | 2 | 0 | 0 | 0 | 0 | 0 | 0 | 0 | 0 | 0 | 0 | 0 | 0 | 0 | 0 | 0 |
| antigen | | | 3 | 0 | 0 | 0 | 0 | 0 | 0 | 0 | 0 | 0 | 0 | 0 | 0 | 0 | 0 | 0 |
| protein of | | coarse | 0 | 6 | 1 | 1 | 3 | 3 | 6 | 6 | 6 | 0 | 6 | 6 | 6 | 6 | 6 | 6 |
| the | | fur | 1 | 0 | 5 | 5 | 3 | 3 | 0 | 0 | 0 | 6 | 0 | 0 | 0 | 0 | 0 | 0 |
| present | | | 2 | 0 | 0 | 0 | 0 | 0 | 0 | 0 | 0 | 0 | 0 | 0 | 0 | 0 | 0 | 0 |
| invention | | | 3 | 0 | 0 | 0 | 0 | 0 | 0 | 0 | 0 | 0 | 0 | 0 | 0 | 0 | 0 | 0 |
| | | death | | 0 | 0 | 0 | 0 | 0 | 0 | 0 | 0 | 0 | 0 | 0 | 0 | 0 | 0 | 0 |
| group 2 | 5 | decrease | 0 | 5 | 0 | 0 | 0 | 0 | 0 | 4 | 4 | 4 | 4 | 4 | 4 | 4 | 4 | 4 |
| H1N1 | | in | 1 | 0 | 4 | 4 | 4 | 4 | 4 | 0 | 0 | 0 | 0 | 0 | 0 | 0 | 0 | 0 |
| virus/ | | activity | 2 | 0 | 0 | 0 | 0 | 0 | 0 | 0 | 0 | 0 | 0 | 0 | 0 | 0 | 0 | 0 |
| solvent | | | 3 | 0 | 0 | 0 | 0 | 0 | 0 | 0 | 0 | 0 | 0 | 0 | 0 | 0 | 0 | 0 |
| | | coarse | 0 | 5 | 0 | 0 | 0 | 0 | 0 | 0 | 3 | 0 | 0 | 0 | 3 | 3 | 3 | 3 |
| | | fur | 1 | 0 | 0 | 0 | 0 | 0 | 3 | 4 | 1 | 4 | 4 | 4 | 1 | 1 | 1 | 1 |
| | | | 2 | 0 | 4 | 4 | 4 | 4 | 1 | 0 | 0 | 0 | 0 | 0 | 0 | 0 | 0 | 0 |
| | | | 3 | 0 | 0 | 0 | 0 | 0 | 0 | 0 | 0 | 0 | 0 | 0 | 0 | 0 | 0 | 0 |
| | | death | | 0 | 1 | 0 | 0 | 0 | 0 | 0 | 0 | 0 | 0 | 0 | 0 | 0 | 0 | 0 |

| group | number of mice | general condition | score | Day (virus inoculaiton day as Day0) 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|
| group 1 | 6 | decrease | 0 | 6 | 6 | 6 | 6 | 5 | 5 | 1 | 0 | 0 | 0 | 0 | 0 | 0 | 2 |
| H1N1 | | in | 1 | 0 | 0 | 0 | 0 | 1 | 0 | 4 | 5 | 5 | 4 | 3 | 2 | 2 | 0 |
| virus/ | | activity | 2 | 0 | 0 | 0 | 0 | 0 | 0 | 0 | 0 | 0 | 0 | 0 | 0 | 0 | 0 |
| antigen | | | 3 | 0 | 0 | 0 | 0 | 0 | 0 | 0 | 0 | 0 | 0 | 0 | 0 | 0 | 0 |
| protein of | | coarse | 0 | 6 | 6 | 5 | 5 | 5 | 2 | 0 | 0 | 0 | 0 | 0 | 0 | 0 | 0 |
| the | | fur | 1 | 0 | 0 | 1 | 1 | 1 | 3 | 5 | 3 | 3 | 0 | 0 | 0 | 0 | 2 |
| present | | | 2 | 0 | 0 | 0 | 0 | 0 | 0 | 0 | 2 | 2 | 4 | 3 | 2 | 2 | 0 |
| invention | | | 3 | 0 | 0 | 0 | 0 | 0 | 0 | 0 | 0 | 0 | 0 | 0 | 0 | 0 | 0 |
| | | death | | 0 | 0 | 0 | 0 | 0 | 1 | 0 | 0 | 0 | 1 | 1 | 1 | 0 | 0 |
| group 2 | 5 | decrease | 0 | 3 | 3 | 0 | 0 | 0 | 0 | 0 | 0 | | | | | | |
| H1N1 | | in | 1 | 1 | 0 | 3 | 3 | 3 | 3 | 0 | 0 | | | | | | |
| virus/ | | activity | 2 | 0 | 0 | 0 | 0 | 0 | 0 | 2 | 0 | | | | | | |
| solvent | | | 3 | 0 | 0 | 0 | 0 | 0 | 0 | 0 | 0 | | | | | | |
| | | coarse | 0 | 1 | 0 | 0 | 0 | 0 | 0 | 0 | 0 | | | | | | |
| | | fur | 1 | 3 | 3 | 3 | 3 | 3 | 2 | 2 | 0 | | | | | | |
| | | | 2 | 0 | 0 | 0 | 0 | 0 | 1 | 0 | 0 | | | | | | |
| | | | 3 | 0 | 0 | 0 | 0 | 0 | 0 | 0 | 0 | | | | | | |
| | | death | | 0 | 1 | 0 | 0 | 0 | 0 | 1 | 2 | | | | | | |

Day 0 virus inoculation day
0: no abnormality, 1: light, 2: moderate, 3: severe

TABLE 2-2

General condition

| group | number of mice | general condition | score | Day (virus inoculation day as Day0) −14 | −13 | −12 | −11 | −10 | −9 | −8 | −7 | −6 | −5 | −4 | −3 | −2 | −1 | 0 |
|---|---|---|---|---|---|---|---|---|---|---|---|---|---|---|---|---|---|---|
| group 3 | 6 | decrease | 0 | 6 | 6 | 6 | 6 | 6 | 6 | 6 | 6 | 6 | 6 | 6 | 6 | 6 | 6 | 6 |
| H3N2 | | in | 1 | 0 | 0 | 0 | 0 | 0 | 0 | 0 | 0 | 0 | 0 | 0 | 0 | 0 | 0 | 0 |
| virus/ | | activity | 2 | 0 | 0 | 0 | 0 | 0 | 0 | 0 | 0 | 0 | 0 | 0 | 0 | 0 | 0 | 0 |
| antigen | | | 3 | 0 | 0 | 0 | 0 | 0 | 0 | 0 | 0 | 0 | 0 | 0 | 0 | 0 | 0 | 0 |
| protein of | | coarse | 0 | 6 | 3 | 3 | 4 | 4 | 6 | 6 | 6 | 0 | 6 | 6 | 6 | 6 | 6 | 6 |
| the | | fur | 1 | 0 | 3 | 3 | 2 | 2 | 0 | 0 | 0 | 6 | 0 | 0 | 0 | 0 | 0 | 0 |
| present | | | 2 | 0 | 0 | 0 | 0 | 0 | 0 | 0 | 0 | 0 | 0 | 0 | 0 | 0 | 0 | 0 |
| invention | | | 3 | 0 | 0 | 0 | 0 | 0 | 0 | 0 | 0 | 0 | 0 | 0 | 0 | 0 | 0 | 0 |
| | | death | | 0 | 0 | 0 | 0 | 0 | 0 | 0 | 0 | 0 | 0 | 0 | 0 | 0 | 0 | 0 |
| group 4 | 5 | decrease | 0 | 5 | 0 | 0 | 0 | 0 | 0 | 3 | 4 | 4 | 4 | 4 | 4 | 4 | 4 | 4 |
| H3N2 | | in | 1 | 0 | 5 | 4 | 4 | 4 | 4 | 1 | 0 | 0 | 0 | 0 | 0 | 0 | 0 | 0 |
| virus/ | | activity | 2 | 0 | 0 | 0 | 0 | 0 | 0 | 0 | 0 | 0 | 0 | 0 | 0 | 0 | 0 | 0 |
| solvent | | | 3 | 0 | 0 | 0 | 0 | 0 | 0 | 0 | 0 | 0 | 0 | 0 | 0 | 0 | 0 | 0 |

TABLE 2-2-continued

| General condition | | | | | | | | | | | | | | | | | | |
|---|---|---|---|---|---|---|---|---|---|---|---|---|---|---|---|---|---|---|
| | | coarse | 0 | 5 | 0 | 0 | 0 | 0 | 0 | 3 | 3 | 0 | 0 | 3 | 4 | 4 | 4 | 4 |
| | | fur | 1 | 0 | 0 | 0 | 2 | 2 | 3 | 1 | 1 | 4 | 4 | 1 | 0 | 0 | 0 | 0 |
| | | | 2 | 0 | 5 | 4 | 2 | 2 | 1 | 0 | 0 | 0 | 0 | 0 | 0 | 0 | 0 | 0 |
| | | | 3 | 0 | 0 | 0 | 0 | 0 | 0 | 0 | 0 | 0 | 0 | 0 | 0 | 0 | 0 | 0 |
| | | death | | 0 | 0 | 1 | 0 | 0 | 0 | 0 | 0 | 0 | 0 | 0 | 0 | 0 | 0 | 0 |

| group | number of mice | general condition | score | Day (virus inoculaiton day as Day0) 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|
| group 3 H3N2 virus/ antigen protein of the present invention | 6 | decrease in activity | 0 | 6 | 6 | 6 | 6 | 6 | 6 | 2 | 2 | 2 | 2 | 2 | 2 | 3 | 3 |
| | | | 1 | 0 | 0 | 0 | 0 | 0 | 0 | 4 | 4 | 3 | 2 | 1 | 1 | 0 | 0 |
| | | | 2 | 0 | 0 | 0 | 0 | 0 | 0 | 0 | 0 | 0 | 0 | 0 | 0 | 0 | 0 |
| | | | 3 | 0 | 0 | 0 | 0 | 0 | 0 | 0 | 0 | 0 | 0 | 0 | 0 | 0 | 0 |
| | | coarse fur | 0 | 6 | 6 | 4 | 4 | 4 | 1 | 0 | 0 | 0 | 0 | 0 | 0 | 2 | 3 |
| | | | 1 | 0 | 0 | 2 | 2 | 2 | 5 | 6 | 3 | 2 | 2 | 2 | 2 | 1 | 0 |
| | | | 2 | 0 | 0 | 0 | 0 | 0 | 0 | 0 | 3 | 3 | 2 | 1 | 1 | 0 | 0 |
| | | | 3 | 0 | 0 | 0 | 0 | 0 | 0 | 0 | 0 | 0 | 0 | 0 | 0 | 0 | 0 |
| | | death | | 0 | 0 | 0 | 0 | 0 | 0 | 0 | 0 | 1 | 1 | 1 | 0 | 0 | 0 |
| group 4 H3N2 virus/ solvent | 5 | decrease in activity | 0 | 4 | 4 | 4 | 3 | 3 | 3 | 0 | 0 | 0 | 0 | 0 | 0 | 0 | |
| | | | 1 | 0 | 0 | 0 | 1 | 0 | 0 | 3 | 3 | 0 | 0 | 0 | 0 | 0 | |
| | | | 2 | 0 | 0 | 0 | 0 | 0 | 0 | 0 | 0 | 3 | 2 | 1 | 1 | 0 | |
| | | | 3 | 0 | 0 | 0 | 0 | 0 | 0 | 0 | 0 | 0 | 0 | 0 | 0 | 0 | |
| | | coarse fur | 0 | 4 | 2 | 2 | 2 | 2 | 0 | 0 | 0 | 0 | 0 | 0 | 0 | 0 | |
| | | | 1 | 0 | 2 | 2 | 2 | 1 | 3 | 3 | 0 | 0 | 0 | 0 | 0 | 0 | |
| | | | 2 | 0 | 0 | 0 | 0 | 0 | 0 | 0 | 3 | 3 | 2 | 1 | 1 | 0 | |
| | | | 3 | 0 | 0 | 0 | 0 | 0 | 0 | 0 | 0 | 0 | 0 | 0 | 0 | 0 | |
| | | death | | 0 | 0 | 0 | 0 | 1 | 0 | 0 | 0 | 0 | 1 | 1 | 0 | 1 | |

Day 0 virus inoculation day
0: no abnormality, 1: light, 2: moderate, 3: severe

TABLE 3

| mouse body weight profile | | | | | | | | |
|---|---|---|---|---|---|---|---|---|
| | group | | | | | | | |
| | group 1 | | group 2 | | group 3 | | group 4 | |
| after virus innoculation (Day) | H1N1/antigen protein of the present invention | (number of animal) | H1N1/ solvent | (number of animal) | H3N2/antigen protein of the present invention | (number of animal) | H3N2/ solvent | (number of animals) |
| arrival date | 19.3 ± 0.8 | (6) | 19.2 ± 1.2 | (5) | 19.0 ± 0.6 | (6) | 19.0 ± 0.5 | (5) |
| Day −14 | 20.5 ± 1.0 | (6) | 20.7 ± 0.7 | (5) | 20.5 ± 1.0 | (6) | 20.8 ± 0.7 | (5) |
| Day −7 | 21.2 ± 1.6 | (6) | 18.1 ± 1.4 | (4) | 21.1 ± 0.8 | (6) | 20.2 ± 2.5 | (4) |
| Day 0 | 21.0 ± 2.2 | (6) | 16.3 ± 1.8 | (4) | 21.4 ± 1.1 | (6) | 19.1 ± 2.8 | (4) |
| Day 3 | 19.5 ± 3.0 | (6) | 15.9 ± 1.6 | (3) | 19.8 ± 1.4 | (6) | 17.7 ± 3.1 | (4) |
| Day 7 | 16.6 ± 1.3 | (5) | 12.7 ± 0.1 | (2) | 15.9 ± 1.4 | (6) | 15.4 ± 0.6 | (3) |
| Day 10 | 14.5 ± 1.1 | (4) | — ± — | (0) | 16.3 ± 2.5 | (4) | 13.6 ± 0.4 | (2) |
| Day 14 | 15.7 ± 0.4 | (2) | — ± — | (0) | 20.1 ± 1.6 | (3) | — ± — | (0) |

(Unit; g)

Mean ± Standard deviation
—: no data due to death in all cases

TABLE 4

| group/administered substance/virus | survival rate after virus inoculation (Day) 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| group 1/antigen protein of the present invention/H1N1 | 100 | 100 | 100 | 100 | 100 | 100 | 83 | 83 | 83 | 83 | 67 | 50 | 33 | 33 | 33 |

TABLE 4-continued

| group/administered substance/virus | survival rate after virus inoculation (Day) 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| group 2/PBS/H1N1 | 100 | 100 | 75 | 75 | 75 | 75 | 75 | 50 | 0 | — | — | — | — | — | — |
| group 3/antigen protein of the present invention/H3N2 | 100 | 100 | 100 | 100 | 100 | 100 | 100 | 100 | 100 | 83 | 67 | 50 | 50 | 50 | 50 |
| group 4/PBS/H3N2 | 100 | 100 | 100 | 100 | 100 | 75 | 75 | 75 | 75 | 75 | 50 | 25 | 25 | 0 | 0 |

(Unit; %)

As shown in Tables 2-1, 2-2, 3, 4, and FIG. 7, the mice inoculated with the antigen protein of the present invention (group 1 and group 3) acquired resistance to influenza virus (H1N1 type and H3N2 type) compared to the groups without inoculation of the antigen protein (group 2 and group 4). Therefore, it was shown that the antigen protein of the present invention is useful as a vaccine capable of conferring cross immunity between influenza A virus subtypes.

INDUSTRIAL APPLICABILITY

The present invention provides an antivirus vaccine that imparts cross immunity effective for a variant virus and a wide range of subtypes. According to the present invention, an effective vaccine that cross-reacts with a wide range of subtypes of influenza A viruses including seasonal influenza virus and predictable highly pathogenic pandemic influenza viruses is expected to be provided.

This application is based on a patent application No. 2017-245606 filed in Japan (filing date: Dec. 21, 2017), the contents of which are incorporated in full herein.

The invention claimed is:

1. A fusion polypeptide that induces a humoral immune response and a cellular immune response to a virus, comprising antigens or fragments thereof of the following (a) and (b), and having an oligomerization activity:

(a) an antigen of the virus or a fragment thereof containing a B cell epitope conserved among subtypes of the virus; and (b) an antigen of the virus or a fragment thereof containing a T cell epitope conserved among subtypes of the virus, wherein the antigen or the fragment thereof of (a) is head-lacking hemagglutinin, wherein the antigen or the fragment thereof of (b) is a matrix protein 1 or a fragment thereof and comprises the amino acid sequence shown in SEQ ID NO: 3, and wherein the antigen or the fragment thereof of (b) has an oligomerization activity.

2. The fusion polypeptide according to claim 1 wherein the virus is an influenza A virus.

3. The fusion polypeptide according to claim 1 comprising a partial sequence consisting of Gln 310-Asp 390 of the amino acid sequence shown in SEQ ID NO: 1.

4. A complex comprising the fusion polypeptide according to claim 1 and a nucleocapsid.

5. A multimer of the fusion polypeptide according to claim 1 that can be formed by oligomerization of the fusion polypeptide.

6. A pharmaceutical composition comprising the fusion polypeptide according to claim 1.

7. A method for inducing an immune response to a virus in a mammal comprising administering an effective amount of the fusion polypeptide according to claim 1 to the mammal.

8. A method for prophylaxis or treatment of an infection with a virus in a mammal comprising administering an effective amount of the fusion polypeptide according to claim 1 to the mammal.

9. A method for producing a pharmaceutical composition for inducing an immune response to a virus or prophylaxis or treatment of an infection with the virus comprising oligomerizing the fusion polypeptide according to claim 1 to give a multimer of the fusion polypeptide.

* * * * *

UNITED STATES PATENT AND TRADEMARK OFFICE

CERTIFICATE OF CORRECTION

PATENT NO. : 11,576,962 B2
APPLICATION NO. : 16/956212
DATED : February 14, 2023
INVENTOR(S) : Sekikawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this
Fourteenth Day of January, 2025

Derrick Brent
*Acting Director of the United States Patent and Trademark Office*

```
                    SEQUENCE LISTING


<160> NUMBER OF SEQ ID NOS: 13

<210> SEQ ID NO 1
<211> LENGTH: 566
<212> TYPE: PRT
<213> ORGANISM: Influenza A virus

<400> SEQUENCE: 1

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125
```

-continued

```
Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Asn Gln Ser Tyr Ile Asn Asp Lys Gly Lys Glu Val Leu Val
            180                 185                 190

Leu Trp Gly Ile His His Pro Ser Thr Thr Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Thr Met Glu Arg Asn Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
```

```
545                 550                 555                 560

Gln Cys Arg Ile Cys Ile
                565


<210> SEQ ID NO 2
<211> LENGTH: 307
<212> TYPE: PRT
<213> ORGANISM: Artificial Sequence
<220> FEATURE:
<223> OTHER INFORMATION: head region-deleted HA

<400> SEQUENCE: 2

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Phe Gln Asn Ile His
65                  70                  75                  80

Pro Ile Thr Ile Gly Lys Cys Pro Lys Tyr Val Lys Ser Thr Lys Leu
                85                  90                  95

Arg Leu Ala Thr Gly Leu Arg Asn Val Pro Ser Ile Gln Ser Arg Gly
            100                 105                 110

Leu Phe Gly Ala Ile Ala Gly Phe Ile Glu Gly Gly Trp Thr Gly Met
        115                 120                 125

Val Asp Gly Trp Tyr Gly Tyr His His Gln Asn Glu Gln Gly Ser Gly
    130                 135                 140

Tyr Ala Ala Asp Leu Lys Ser Thr Gln Asn Ala Ile Asp Lys Ile Thr
145                 150                 155                 160

Asn Lys Val Asn Ser Val Ile Glu Lys Met Asn Thr Gln Phe Thr Ala
                165                 170                 175

Val Gly Lys Glu Phe Asn His Leu Glu Lys Arg Ile Glu Asn Leu Asn
            180                 185                 190

Lys Lys Val Asp Asp Gly Phe Leu Asp Ile Trp Thr Tyr Asn Ala Glu
        195                 200                 205

Leu Leu Val Leu Leu Glu Asn Glu Arg Thr Leu Asp Tyr His Asp Ser
    210                 215                 220

Asn Val Lys Asn Leu Tyr Glu Lys Val Arg Asn Gln Leu Lys Asn Asn
225                 230                 235                 240

Ala Lys Glu Ile Gly Asn Gly Cys Phe Glu Phe Tyr His Lys Cys Asp
                245                 250                 255

Asn Thr Cys Met Glu Ser Val Lys Asn Gly Thr Tyr Asp Tyr Pro Lys
            260                 265                 270

Tyr Ser Glu Glu Ala Lys Leu Asn Arg Glu Lys Ile Asp Gly Val Lys
        275                 280                 285

Leu Glu Ser Thr Arg Ile Tyr Cys Ser Asn Gly Ser Leu Gln Cys Arg
    290                 295                 300

Ile Cys Ile
305


<210> SEQ ID NO 3
<211> LENGTH: 9
<212> TYPE: PRT
```

-continued

<213> ORGANISM: Artificial Sequence
<220> FEATURE:
<223> OTHER INFORMATION: T-cell epitope in M1

<400> SEQUENCE: 3

Gly Ile Leu Gly Phe Val Phe Thr Leu
1               5

<210> SEQ ID NO 4
<211> LENGTH: 252
<212> TYPE: PRT
<213> ORGANISM: Influenza A virus

<400> SEQUENCE: 4

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Ser Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Ile
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Ala Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Thr Thr Asn Pro Leu Ile Arg His Glu
                165                 170                 175

Asn Arg Met Val Leu Ala Ser Thr Thr Ala Lys Ala Met Glu Gln Val
            180                 185                 190

Ala Gly Ser Ser Glu Gln Ala Ala Glu Ala Met Glu Val Ala Asn Lys
        195                 200                 205

Thr Arg Gln Met Val His Ala Met Arg Thr Ile Gly Thr His Pro Ser
    210                 215                 220

Ser Ser Ala Gly Leu Arg Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 5
<211> LENGTH: 9
<212> TYPE: PRT
<213> ORGANISM: Artificial Sequence
<220> FEATURE:
<223> OTHER INFORMATION: T-cell epitope in NP

<400> SEQUENCE: 5

Ser Arg Tyr Trp Ala Ile Arg Thr Arg
1               5

-continued

<210> SEQ ID NO 6
<211> LENGTH: 498
<212> TYPE: PRT
<213> ORGANISM: Influenza A virus

<400> SEQUENCE: 6

```
Met Ala Ser Gln Gly Thr Lys Arg Ser Tyr Glu Gln Met Glu Thr Gly
1               5                   10                  15

Gly Glu Arg Gln Asp Thr Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Asp Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Thr Arg Glu Leu Ile Leu Tyr Asp
            100                 105                 110

Lys Glu Glu Ile Arg Arg Val Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Val Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
    290                 295                 300

Lys Leu Leu Gln Asn Ser Gln Val Val Ser Leu Met Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Lys Lys Val
            340                 345                 350

Ile Pro Arg Gly Lys Leu Ser Thr Arg Gly Val Gln Ile Ala Ser Asn
        355                 360                 365

Glu Asn Val Glu Thr Met Asp Ser Asn Thr Leu Glu Leu Arg Ser Arg
    370                 375                 380
```

```
Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Val Met Ala Ala Phe Ser Gly Asn
            420                 425                 430

Asn Glu Gly Arg Thr Ser Asp Met Arg Thr Glu Val Ile Arg Met Met
        435                 440                 445

Glu Ser Ala Lys Pro Glu Asp Leu Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 7
<211> LENGTH: 79
<212> TYPE: PRT
<213> ORGANISM: Artificial Sequence
<220> FEATURE:
<223> OTHER INFORMATION: M1 oligomerization sequence

<400> SEQUENCE: 7

Asn Gly Asp Pro Asn Asn Met Asp Arg Ala Val Lys Leu Tyr Lys Lys
1               5                   10                  15

Leu Lys Arg Glu Ile Thr Phe His Gly Ala Lys Glu Val Ser Leu Ser
            20                  25                  30

Tyr Ser Thr Gly Ala Leu Ala Ser Cys Met Gly Leu Ile Tyr Asn Arg
        35                  40                  45

Met Gly Thr Val Thr Thr Glu Ala Ala Phe Gly Leu Val Cys Ala Thr
    50                  55                  60

Cys Glu Gln Ile Ala Asp Ser Gln His Arg Ser His Arg Gln Met
65                  70                  75


<210> SEQ ID NO 8
<211> LENGTH: 775
<212> TYPE: PRT
<213> ORGANISM: Artificial Sequence
<220> FEATURE:
<223> OTHER INFORMATION: HA-M1 fusion protein

<400> SEQUENCE: 8

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110
```

-continued

```
Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Asn Gln Ser Tyr Ile Asn Asp Lys Gly Lys Glu Val Leu Val Leu
                165                 170                 175

Trp Gly Ile His His Pro Ser Thr Thr Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

Lys Phe Lys Pro Glu Ile Ala Thr Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Glu Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Lys Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Asn Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Lys Ile Asp Gly Val Lys Leu Glu Ser Thr Arg Ile Tyr Cys
            500                 505                 510

Ser Asn Gly Ser Leu Gln Cys Arg Ile Cys Ile Met Ser Leu Leu Thr
        515                 520                 525

Glu Val Glu Thr Tyr Val Leu Ser Ile Ile Pro Ser Gly Pro Leu Lys
```

```
    530                 535                 540

Ala Glu Ile Ala Gln Arg Leu Glu Ser Val Phe Ala Gly Lys Asn Thr
545                 550                 555                 560

Asp Leu Glu Ala Leu Met Glu Trp Leu Lys Thr Arg Pro Ile Leu Ser
                565                 570                 575

Pro Leu Thr Lys Gly Ile Leu Gly Phe Val Phe Thr Leu Thr Val Pro
            580                 585                 590

Ser Glu Arg Gly Leu Gln Arg Arg Arg Phe Ile Gln Asn Ala Leu Asn
        595                 600                 605

Gly Asn Gly Asp Pro Asn Asn Met Asp Arg Ala Val Lys Leu Tyr Lys
    610                 615                 620

Lys Leu Lys Arg Glu Ile Thr Phe His Gly Ala Lys Glu Val Ser Leu
625                 630                 635                 640

Ser Tyr Ser Thr Gly Ala Leu Ala Ser Cys Met Gly Leu Ile Tyr Asn
                645                 650                 655

Arg Met Gly Thr Val Thr Thr Glu Ala Ala Phe Gly Leu Val Cys Ala
            660                 665                 670

Thr Cys Glu Gln Ile Ala Asp Ser Gln His Arg Ser His Arg Gln Met
        675                 680                 685

Ala Thr Thr Thr Asn Pro Leu Ile Arg His Glu Asn Arg Met Val Leu
    690                 695                 700

Ala Ser Thr Thr Ala Lys Ala Met Glu Gln Val Ala Gly Ser Ser Glu
705                 710                 715                 720

Gln Ala Ala Glu Ala Met Glu Val Ala Asn Lys Thr Arg Gln Met Val
                725                 730                 735

His Ala Met Arg Thr Ile Gly Thr His Pro Ser Ser Ser Ala Gly Leu
            740                 745                 750

Arg Asp Asp Leu Leu Glu Asn Leu Gln Ala Tyr Gln Lys Arg Met Gly
        755                 760                 765

Val Gln Met Gln Arg Phe Lys
    770                 775


<210> SEQ ID NO 9
<211> LENGTH: 542
<212> TYPE: PRT
<213> ORGANISM: Artificial Sequence
<220> FEATURE:
<223> OTHER INFORMATION: head-deleted HA-M1 fusion protein

<400> SEQUENCE: 9

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Phe Gln Asn Ile His Pro
    50                  55                  60

Ile Thr Ile Gly Lys Cys Pro Lys Tyr Val Lys Ser Thr Lys Leu Arg
65                  70                  75                  80

Leu Ala Thr Gly Leu Arg Asn Val Pro Ser Ile Gln Ser Arg Gly Leu
                85                  90                  95

Phe Gly Ala Ile Ala Gly Phe Ile Glu Gly Gly Trp Thr Gly Met Val
            100                 105                 110

Asp Gly Trp Tyr Gly Tyr His His Gln Asn Glu Gln Gly Ser Gly Tyr
```

```
        115                 120                 125

Ala Ala Asp Leu Lys Ser Thr Gln Asn Ala Ile Asp Lys Ile Thr Asn
    130                 135                 140

Lys Val Asn Ser Val Ile Glu Lys Met Asn Thr Gln Phe Thr Ala Val
145                 150                 155                 160

Gly Lys Glu Phe Asn His Leu Glu Lys Arg Ile Glu Asn Leu Asn Lys
                165                 170                 175

Lys Val Asp Asp Gly Phe Leu Asp Ile Trp Thr Tyr Asn Ala Glu Leu
            180                 185                 190

Leu Val Leu Leu Glu Asn Glu Arg Thr Leu Asp Tyr His Asp Ser Asn
        195                 200                 205

Val Lys Asn Leu Tyr Glu Lys Val Arg Asn Gln Leu Lys Asn Asn Ala
    210                 215                 220

Lys Glu Ile Gly Asn Gly Cys Phe Glu Phe Tyr His Lys Cys Asp Asn
225                 230                 235                 240

Thr Cys Met Glu Ser Val Lys Asn Gly Thr Tyr Asp Tyr Pro Lys Tyr
                245                 250                 255

Ser Glu Glu Ala Lys Leu Asn Arg Glu Lys Ile Asp Gly Val Lys Leu
            260                 265                 270

Glu Ser Thr Arg Ile Tyr Cys Ser Asn Gly Ser Leu Gln Cys Arg Ile
        275                 280                 285

Cys Ile Met Ser Leu Leu Thr Glu Val Glu Thr Tyr Val Leu Ser Ile
    290                 295                 300

Ile Pro Ser Gly Pro Leu Lys Ala Glu Ile Ala Gln Arg Leu Glu Ser
305                 310                 315                 320

Val Phe Ala Gly Lys Asn Thr Asp Leu Glu Ala Leu Met Glu Trp Leu
                325                 330                 335

Lys Thr Arg Pro Ile Leu Ser Pro Leu Thr Lys Gly Ile Leu Gly Phe
            340                 345                 350

Val Phe Thr Leu Thr Val Pro Ser Glu Arg Gly Leu Gln Arg Arg Arg
        355                 360                 365

Phe Ile Gln Asn Ala Leu Asn Gly Asn Gly Asp Pro Asn Asn Met Asp
    370                 375                 380

Arg Ala Val Lys Leu Tyr Lys Lys Leu Lys Arg Glu Ile Thr Phe His
385                 390                 395                 400

Gly Ala Lys Glu Val Ser Leu Ser Tyr Ser Thr Gly Ala Leu Ala Ser
                405                 410                 415

Cys Met Gly Leu Ile Tyr Asn Arg Met Gly Thr Val Thr Thr Glu Ala
            420                 425                 430

Ala Phe Gly Leu Val Cys Ala Thr Cys Glu Gln Ile Ala Asp Ser Gln
        435                 440                 445

His Arg Ser His Arg Gln Met Ala Thr Thr Thr Asn Pro Leu Ile Arg
    450                 455                 460

His Glu Asn Arg Met Val Leu Ala Ser Thr Thr Ala Lys Ala Met Glu
465                 470                 475                 480

Gln Val Ala Gly Ser Ser Glu Gln Ala Ala Glu Ala Met Glu Val Ala
                485                 490                 495

Asn Lys Thr Arg Gln Met Val His Ala Met Arg Thr Ile Gly Thr His
            500                 505                 510

Pro Ser Ser Ser Ala Gly Leu Arg Asp Asp Leu Leu Glu Asn Leu Gln
        515                 520                 525

Ala Tyr Gln Lys Arg Met Gly Val Gln Met Gln Arg Phe Lys
    530                 535                 540
```

<210> SEQ ID NO 10
<211> LENGTH: 1695
<212> TYPE: DNA
<213> ORGANISM: Artificial Sequence
<220> FEATURE:
<223> OTHER INFORMATION: Polynucleotide sequence encoding head-deleted HA-M1 fusion protein with GS linker and 6xHis tag

<400> SEQUENCE: 10

```
atggacacat tatgtatagg ttatcatgcg aacaattcaa cagacactgt agacacagta     60
ctagaaaaga atgtaacagt aacacactct gttaaccttc tggaagacaa gcataacgga    120
aaactatgca aactaagagg ggtagcccca ttgcatttgg gtaaatgtaa cattgctggt    180
ggaggaggtt ctggtggagg aggttctggt ggaggaggtt cttttcagaa tatacatccg    240
atcacaattg gaaaatgtcc aaagtatgta aaaagcacaa aattgagact ggccacagga    300
ttgaggaatg ttccgtctat tcaatctaga ggcctattcg gggccattgc cggcttcatt    360
gaagggggggt ggacagggat ggtagatgga tggtacggtt atcaccatca aaatgagcag    420
gggtcaggat atgcagccga cctgaagagc acacaaaatg ccattgacaa gattactaac    480
aaagtaaatt ctgttattga aaagatgaat acacagttca cagcagtggg taaagagttc    540
aaccacctgg aaaaaagaat agagaatcta aataaaaaag ttgatgatgg tttcctggac    600
atttggactt acaatgccga actgttggtt ctattggaaa atgaaagaac tttggactat    660
cacgattcaa atgtgaagaa cttgtatgaa aaagtaagaa accagttaaa aaacaatgcc    720
aaggaaattg gaaacggctg ctttgaattt taccacaaat gcgataacac gtgcatggaa    780
agtgtcaaaa atgggactta tgactaccca aaatactcag aggaagcaaa attaaacaga    840
gaaaaaatag atggggtaaa gctggaatca acaaggattt actgctctaa tgggtctcta    900
cagtgtagaa tatgtattat gagtcttcta accgaggtcg aaacgtatgt tctctctatc    960
gtcccgtcag gcccccctcaa agccgagata gcacagagac tcgaagacgt ttttgcaggg   1020
aaaaacaccg atcttgaggc tctcatggaa tggctaaaga caagaccaat cttgtcacct   1080
ctgactaagg ggattttagg gtttgtgttc acgctcaccg tgcccagtga gcgaggactg   1140
cagcgtagac gttttgtcca gaatgccctc aatgggaatg gtgacccgaa caacatggac   1200
aaggcggtca aactgtacag gaaactaaaa agggagataa cattccatgg ggccaaagaa   1260
gtagcgctca gttactctgc tggtgcactt gccagttgca tgggcctcat atacaacaga   1320
atggggactg tcaccactga ggtggccttt ggtctggtat gcgcaacctg tgaacagatt   1380
gctgattctc agcatcgatc tcatagacaa atggtgacaa caaccaatcc actaatcagg   1440
cacgagaaca gaatggtaat agccagcaca acagctaaag ccatggaaca aatggctgga   1500
tcaagcgaac aagcagcaga ggctatggag gttgccagcc aggctagaca aatggtacag   1560
gcaatgagaa caattgggac tcaccctagt tccagcactg gtctaaaaga tgatctcctt   1620
gaaaatttac aggcctatca gaaacggatg ggagtgcaaa tgcaacgatt caaacatcat   1680
catcatcatc actga                                                    1695
```

<210> SEQ ID NO 11
<211> LENGTH: 564
<212> TYPE: PRT
<213> ORGANISM: Artificial Sequence
<220> FEATURE:
<223> OTHER INFORMATION: Amino acid sequence of head-deleted HA-M1 fusion protein with GS linker and 6xHis tag -continued

<400> SEQUENCE: 11

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30

Leu Leu Glu Asp Lys His Asn Gly Lys Leu Cys Lys Leu Arg Gly Val
        35                  40                  45

Ala Pro Leu His Leu Gly Lys Cys Asn Ile Ala Gly Gly Gly Gly Ser
    50                  55                  60

Gly Gly Gly Gly Ser Gly Gly Gly Gly Ser Phe Gln Asn Ile His Pro
65                  70                  75                  80

Ile Thr Ile Gly Lys Cys Pro Lys Tyr Val Lys Ser Thr Lys Leu Arg
                85                  90                  95

Leu Ala Thr Gly Leu Arg Asn Val Pro Ser Ile Gln Ser Arg Gly Leu
            100                 105                 110

Phe Gly Ala Ile Ala Gly Phe Ile Glu Gly Gly Trp Thr Gly Met Val
        115                 120                 125

Asp Gly Trp Tyr Gly Tyr His His Gln Asn Glu Gln Gly Ser Gly Tyr
    130                 135                 140

Ala Ala Asp Leu Lys Ser Thr Gln Asn Ala Ile Asp Lys Ile Thr Asn
145                 150                 155                 160

Lys Val Asn Ser Val Ile Glu Lys Met Asn Thr Gln Phe Thr Ala Val
                165                 170                 175

Gly Lys Glu Phe Asn His Leu Glu Lys Arg Ile Glu Asn Leu Asn Lys
            180                 185                 190

Lys Val Asp Asp Gly Phe Leu Asp Ile Trp Thr Tyr Asn Ala Glu Leu
        195                 200                 205

Leu Val Leu Leu Glu Asn Glu Arg Thr Leu Asp Tyr His Asp Ser Asn
    210                 215                 220

Val Lys Asn Leu Tyr Glu Lys Val Arg Asn Gln Leu Lys Asn Asn Ala
225                 230                 235                 240

Lys Glu Ile Gly Asn Gly Cys Phe Glu Phe Tyr His Lys Cys Asp Asn
                245                 250                 255

Thr Cys Met Glu Ser Val Lys Asn Gly Thr Tyr Asp Tyr Pro Lys Tyr
            260                 265                 270

Ser Glu Glu Ala Lys Leu Asn Arg Glu Lys Ile Asp Gly Val Lys Leu
        275                 280                 285

Glu Ser Thr Arg Ile Tyr Cys Ser Asn Gly Ser Leu Gln Cys Arg Ile
    290                 295                 300

Cys Ile Met Ser Leu Leu Thr Glu Val Glu Thr Tyr Val Leu Ser Ile
305                 310                 315                 320

Val Pro Ser Gly Pro Leu Lys Ala Glu Ile Ala Gln Arg Leu Glu Asp
                325                 330                 335

Val Phe Ala Gly Lys Asn Thr Asp Leu Glu Ala Leu Met Glu Trp Leu
            340                 345                 350

Lys Thr Arg Pro Ile Leu Ser Pro Leu Thr Lys Gly Ile Leu Gly Phe
        355                 360                 365

Val Phe Thr Leu Thr Val Pro Ser Glu Arg Gly Leu Gln Arg Arg Arg
    370                 375                 380

Phe Val Gln Asn Ala Leu Asn Gly Asn Gly Asp Pro Asn Asn Met Asp
385                 390                 395                 400

Lys Ala Val Lys Leu Tyr Arg Lys Leu Lys Arg Glu Ile Thr Phe His
                405                 410                 415

-continued

```
Gly Ala Lys Glu Val Ala Leu Ser Tyr Ser Ala Gly Ala Leu Ala Ser
            420                 425                 430

Cys Met Gly Leu Ile Tyr Asn Arg Met Gly Thr Val Thr Thr Glu Val
        435                 440                 445

Ala Phe Gly Leu Val Cys Ala Thr Cys Glu Gln Ile Ala Asp Ser Gln
    450                 455                 460

His Arg Ser His Arg Gln Met Val Thr Thr Thr Asn Pro Leu Ile Arg
465                 470                 475                 480

His Glu Asn Arg Met Val Ile Ala Ser Thr Thr Ala Lys Ala Met Glu
            485                 490                 495

Gln Met Ala Gly Ser Ser Glu Gln Ala Ala Glu Ala Met Glu Val Ala
            500                 505                 510

Ser Gln Ala Arg Gln Met Val Gln Ala Met Arg Thr Ile Gly Thr His
        515                 520                 525

Pro Ser Ser Ser Thr Gly Leu Lys Asp Asp Leu Leu Glu Asn Leu Gln
    530                 535                 540

Ala Tyr Gln Lys Arg Met Gly Val Gln Met Gln Arg Phe Lys His His
545                 550                 555                 560

His His His His


<210> SEQ ID NO 12
<211> LENGTH: 15
<212> TYPE: PRT
<213> ORGANISM: Artificial Sequence
<220> FEATURE:
<223> OTHER INFORMATION: GS linker

<400> SEQUENCE: 12

Gly Gly Gly Gly Ser Gly Gly Gly Gly Ser Gly Gly Gly Gly Ser
1               5                   10                  15


<210> SEQ ID NO 13
<211> LENGTH: 6
<212> TYPE: PRT
<213> ORGANISM: Artificial Sequence
<220> FEATURE:
<223> OTHER INFORMATION: 6xHis tag

<400> SEQUENCE: 13

His His His His His His
1               5
```